(12) United States Patent
Kubota et al.

(10) Patent No.: US 7,833,798 B2
(45) Date of Patent: Nov. 16, 2010

(54) METHOD FOR ANALYSIS OF ALBUMIN IN SAMPLE SOLUTION

(75) Inventors: Kazuyuki Kubota, Kawasaki (JP); Naoyuki Yamada, Kawasaki (JP); Kenji Takehana, Kawasaki (JP); Asami Kawakami, Kawasaki (JP); Akira Nakayama, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 12/019,675

(22) Filed: Jan. 25, 2008

(65) Prior Publication Data

US 2008/0138846 A1 Jun. 12, 2008

Related U.S. Application Data

(63) Continuation of application No. PCT/JP2006/315358, filed on Jul. 27, 2006.

(30) Foreign Application Priority Data

Jul. 27, 2005 (JP) ............................ 2005-217993

(51) Int. Cl.
  *G01N 33/50* (2006.01)
  *G01N 33/00* (2006.01)
  *C12Q 1/37* (2006.01)
(52) U.S. Cl. ............................ 436/88; 436/87; 436/86; 435/23; 435/18; 435/4
(58) Field of Classification Search .................. 436/88, 436/86, 87; 435/23, 18, 4
See application file for complete search history.

(56) References Cited

U.S. PATENT DOCUMENTS

2005/0147720 A1  7/2005  Yamada et al.

FOREIGN PATENT DOCUMENTS

| JP | 61155397 | 7/1986 |
| JP | 2003139751 | 5/2003 |

OTHER PUBLICATIONS

Machine Translation of JP 2003 139751. Yoshifumi et al., Substance for Controlling Precision, 2003.*
Wantanbe A. et al., Problems in Serum Albumin Measurement and Clinical Significance of Albumin Microhetergeneity in Cirrhotics, Nutrition, 2004, 20: 351-357.*
Botting, C. H., "The use of the slow crystallization method to improve matrix-assisted laser desorption/ionization time-of-flight signals for larger proteins," Rapid Communications in Mass Spectroscopy 2000;14(21):2030-2033.
Cabrera-Crespo, J., et al., "Albumin purification from human placenta," Biotechnol. Appl. Biochem. Apr. 2000;31, Part 2:101-106.
Kato, Y., et al., "Separation of Human Serum Proteins by High-Speed Gel Filtration on TSK-GEL G3000SWG," J. of HRC & CC 1980;3(3):145.
Sogami, M., et al., "High-Performance Liquid Chromatographic Studies on Non-Mercapt Mercapt Conversion of Human Serum Albumin. II" J. Chroma. 1985;332:19-27.
Wang, H. L., et al., "Determination of Drug-Protein Interactions by Combined Microdialysis and High-Performance Liquid Chromatography," Chromatographia 1997;44(3/4):205-208.
Wang, H., et al., "Multi-Site Binding of Fenoprofen to Human Serum Albumin Studied by a Combined Technique of Microdialysis with High Performance Liquid Chromatography," Biomed. Chromatography 1998;12(1):4-7.
Watanabe, A., "Heterogenicity of serum albumin and its clinical significance," Pharma Medica, 2001 Nen 3 Gatsu 10 Hakko;19(3):195-204.
Ye, S-F, et al., "Protective Effects of Shojusen on the Endocrine Disturbances Induced by Oxidative Stress," Dokkyo J. Med. Sci., 2004 Nen 3 Gatsu 25 Nichi Hakko; 31(1):91-97.
International Search Report for PCT Patent App. No. PCT/JP2006/315358 (Oct. 31, 2006).

* cited by examiner

*Primary Examiner*—Vickie Kim
*Assistant Examiner*—Christine T Mui
(74) *Attorney, Agent, or Firm*—Shelly Guest Cermak; Cermak Nakajima LLP

(57) ABSTRACT

The present invention provides a method of analyzing albumin in a sample solution, which is characterized by pretreating a sample solution before subjecting the sample solution to mass spectrometry or liquid chromatography. The present invention further provides a method of accurately and stably analyzing the amount and ratio of oxidized and reduced albumin in a sample solution, and an albumin standard accurate and controlled quantitative analysis of albumin.

15 Claims, 10 Drawing Sheets

METHOD FOR ANALYSIS OF ALBUMIN IN SAMPLE SOLUTION

This application claims priority under 35 U.S.C. §119 to Japanese Patent Application No. 2005-217993, filed Jul. 27, 2005, and is a continuation under 35 U.S.C. §120 of PCT Patent Application No. PCT/JP2006/315358, filed on Jul. 27, 2006, the entireties of which are incorporated by reference.

BACKGROUND OF THE INVENTION

1. Field of the Invention

The present invention relates to a method of analyzing albumin in a sample solution by mass spectrometry or liquid chromatography. More particularly, the present invention relates to a method of analyzing albumin in a sample solution, which is characterized by pre-treating the sample solution before subjecting it to mass spectrometry or liquid chromatography. Furthermore, the present invention relates to an accurate and stable method of determining the amount of, and hence the ratio of, oxidized and reduced albumin in a sample solution. Finally, the present invention relates to an albumin standard which controls the accuracy of the quantitative analysis of albumin.

2. Brief Description of the Related Art

Albumin is a protein widely and ubiquitously distributed in living bodies. Human albumin is a simple protein consisting of 585 amino acids, a molecular weight of 66 kDa, 17 disulfide bonds, and a single free cysteine per molecule. Albumin is produced in the liver and secreted into blood, and accounts for about 60% of the total protein present in plasma. Albumin is known to exhibit the following physiological effects: (1) control and maintenance of the plasma osmotic pressure, (2) transport of bilirubin, amino acids, fatty acids, hormones, metal ions, drugs, and the like, (3) a source of amino acids during malnutrition, (4) redox buffering ability, and the like. Particularly, the bond between a drug and albumin significantly affects the efficacy of the drug. As described, albumin is a protein having various functions.

Reduced albumin, oxidized albumin, glycated albumin, and the like are known to be present heterogeneously within the living body. In particular, significant albumin glycation is generally reported in diabetes (Suzuki E., Diabetes Res. 18(3), 153-158, 1992), and the amount of glycated albumin formed by glucose binding is being considered for use as a marker for monitoring blood glucose levels clinically, like hemoglobin A1c in diabetics.

However, the presence of reduced albumin (Alb(red)) and oxidized albumin (Alb(ox)) has also recently been shown to be an indicator of various diseases. For example, it has been shown that the structure of Alb(red) in the blood includes a free SH group in the 34th cysteine, as measured from the N-terminus. It has also been shown that the Alb(ox) present in the blood can add a sulfur-containing compound such as cysteine, and the like, in vivo via a disulfide bond to the SH group of the 34th cysteine (Era S, Int. J. Peptide Protein Res. 31, 435-422, 1988).

Alb(red) and Alb(ox) exist in vivo in dynamic equilibrium, as the disulfide bond reversibly forms and dissociates quickly. Accordingly, the ratio of Alb(red) to Alb(ox) in plasma indicates the redox state in blood. That is, when some oxidative stress occurs, the amount of Alb(ox) increases. Specifically, Alb(ox) is known to increase in elderly persons, patients with nephrosis syndrome, dialysis, hepatic diseases, and the like (Sogami M., J. Chromatogr., 332, 19-27, 1985; Akiharu Watanabe, Phama Medica, 19, 195-204, 2001; Suzuki E, Diabetes Res Clin Pract, 18, 153-158, 1992). In addition, diabetic patients are considered to be under oxidative stress due to increased blood oxidative products, decreased antioxidant enzyme activity, and formation of a free radical resulting in microvascular damage (Oberley L W, Free Radical Biol. Med., 5, 113-124, 1988).

When the oxidation and antioxidation reactions are not in balance and the oxidation reaction prevails, a body undergoes oxidative stress, which can be damaging. For example, cellular DNA, phospholipids on cellular membranes, proteins, and carbohydrates are damaged due to oxidative stress, resulting in advanced angiopathy, which aggravates various health conditions. As a result, oxidative stress is said to cause aging and various diseases, and it is known that substances having an antioxidant effect, such as polyphenol and the like, are good for health. Accordingly, the ability to easily monitor oxidized conditions in vivo will enable the monitoring of health conditions, and the screening for drugs and health materials.

Cirrhosis has been identified as a disease in which oxidized albumin increases. In cirrhosis patients, the blood albumin level decreases since the liver's ability to produce albumin is degraded. Preparations of human plasma albumin and branched chain amino acids are used to treat hypoalbuminemia. In hepatic diseases such as cirrhosis and the like, a decrease in the albumin level as well as an increase in oxidized albumin are observed (Watanabe A, Netrition 20, 351-357, 2004).

Moreover, fluctuation of redox balancing due to oxidative stress also occurs by impairment of renal function (Terawaki H., Kidney Int. 65(5), 1988-1993, 2004), diabetes (Suzuki E., Diabetes Res. 18(3), 153-158, 1992), rheumatism (Narazaki R., Arch. Toxicol. 14, 351-353, 1998), aging (Era S., Biochim. Biophys. Acta., 1247(1), 12-16, 1995), and the like.

In this way, albumin buffers the ability to undergo a redox reaction by forming a reductant/oxidant by itself. Accordingly, the ratio of oxidized albumin to reduced albumin is considered to reflect the redox state. Therefore, once the reduced/oxidized albumin ratio of the blood can be accurately determined in vivo, the therapeutic effect on a disease or health condition caused by oxidative stress, or the course of the disease or health condition, can be monitored.

There are several methods for determining the ratio of Alb(red) to Alb(ox), including using dye-binding to quantitatively measure the albumin. The two kinds of dye that may be used in this method are bromcresol green (BCG) and bromcresol purple (BCP). Since different reactivities of Alb (red) and Alb(ox) are obtained when using BCP, the difference in the amount of albumin quantitatively determined using BCP versus BCG indicates the ratio of Alb(ox). However, this method gives poor quanititative results and, therefore, is not reliable.

In addition, the Alb(red)-derived SH group may be quantified using a free-SH group quantitative reagent such as Ellman's Reagent, and the like (Sogami M, Int. Pept. Protein Res., 24(2), 96-103, 1984). However, this method fails to distinguish between albumin and substances with an other types of SH group.

Currently, the best method for quantifying reduced and oxidized albumin is high performance liquid chromatography (HPLC) (Sogami M., J. Chromatogr., 332, 19-27, 1985; JP-A-61-155397; JP-B-2-4863). When analyzing serum albumin using HPLC, reduced albumin (Alb(red)) and oxidized albumin (Alb(ox)) can be separately detected. The ratio of the amount of Alb(red) to the total combined amount of Alb(red) and Alb(ox) (Alb(red) %=peak area of Alb(red)/ peak area of (Alb(red)+peak area of Alb(ox))×100) can be determined from the peak area ratio on the chromatogram.

However, there are some problems with HPLC, including maintaining the stability of the sample. Since reduced albumin in plasma is highly unstable, the amount of oxidized albumin increases due to natural oxidation, even when preserved at −20° C., and the amount of Alb(red) decreases. This reaction occurs in parallel with the temperature rise. Accordingly, plasma should be stored at −70° C. or below (Ryozo Muramoto, *Igaku no Ayumi*, 198(13), 972-976, 2001). For HPLC, the plasma stored at −70° C. or below should be thawed and immediately thereafter applied to the HPLC.

A second problem which can occur is insufficient separation of Alb(red) and Alb(ox). Since Alb(red) and Alb(ox) have only minor structural differences, it is extremely difficult to completely separate them by HPLC, and baseline separation on a chromatogram is unattainable (Keiko Yasukawa, *Rinsyou Kensa*, 44(8), 907-910, 2000). A third problem is that the exact structure of oxidized albumin cannot be detected. In Alb(ox), a sulfur-containing compound such as cysteine, glutathione, and the like, bonds to the 34th cysteine from the N-terminus of albumin via a disulfide bond. This structure of Alb(ox) cannot be specifically recognized using HPLC.

Recently, analysis of albumin using a mass spectrometer was reported to potentially be successful for overcoming the above-mentioned second and third problems (Keiko Yasukawa, *Rinsyou Kensa*, 44(8), 907-910, 2000). The advances in mass spectrometry are remarkable in recent years, and it is becoming possible to measure a protein having a large molecular weight with high accuracy and high mass resolution. Alb(ox) is heavier than Alb(red) due to the mass of the additional compound, for example, cysteine. Accordingly, Alb(red) and Alb(ox) can be separately detected by a mass spectrometer having sufficient mass resolution. In the above-mentioned literature, Yasukawa et al. measured the amount of albumin in healthy subjects and diabetic patients with an electrospray ionization mass spectrometer (ESI-MS), and was able to detect Alb(red) and Alb(ox), as well as glycated albumin.

However, the above-mentioned problem regarding the instability of reduced albumin in plasma remains a serious obstacle in the ESI-MS method. Since the ratio of oxidized albumin in plasma increases during storage above −70° C., preservation of samples is difficult. Moreover, since the amount of oxidized albumin is steadily increasing during thawing, and up to the point of measurement of the once frozen plasma, fluctuation of the measurement can occur, and inaccurate results are obtained. Accordingly, plasma kept at −70° C. or below should be thawed and immediately thereafter subjected to HPLC or ESI-MS. The time and room temperature during thawing can cause variation in the Alb(red) % value. Furthermore, substances typically used to enhance accuracy of the analysis cannot be stably preserved, therefore, control of the accuracy of the analysis is extremely difficult. In addition, automation of the analysis using an auto injector is difficult. Therefore, the measurement of the ratio of reduced albumin to oxidized albumin is not commonly practiced, but is practiced only in particular research institutions. Furthermore, while serum albumin is typically quantified by the dye-binding method, accurate quantification is problematic and therefore unavailable due to the difference in the reactions of oxidized and reduced albumins (Ryozo Muramoto, *Rinsyou Kensa*, 48(5), 537-544, 2004).

Generally, in analytical methods, standardized samples are important to ensure accuracy and precision. Oxidized albumin is prepared in a test tube by reacting it with a compound having a thiol group, such as cysteine, glutathione, and the like (Gabaldon M., *Arch. Biochem. Biophys.* 431, 178-188, 2004). However, as mentioned above, since this reaction is reversible, at oxidized albumin is easily converted to reduced albumin. Accordingly, a standardized sample which is able to maintain a constant ratio of the oxidized and reduced albumins has been desired for a long time, so that analysis can be performed with high accuracy.

SUMMARY OF THE INVENTION

The present inventors have conducted intensive studies and found that albumin in a sample solution can be stabilized by adjusting the pH of the sample solution to a particular range, preferably by diluting the sample to achieve a pH within the desired range, or by removing low-molecular compounds by affinity chromatography, gel filtration chromatography, ultrafiltration, and the like. This method affords marked suppression of the oxidization of reduced albumin in the sample solution, and enables a more stable and highly accurate albumin measurement when the stabilized solution is subjected to mass spectrometry or liquid chromatography directly or after filtration, as compared to previously described methods.

Accordingly, aspects of the present invention are as follows.

It is an aspect of the present invention to provide a method of analyzing albumin in a sample solution, the method comprising A) adjusting the pH of the sample solution to pH 4-9, and B) subjecting the sample solution to an analytical technique selected from the group consisting of mass spectrometry and liquid chromatography.

It is a further aspect of the present invention to provide the method as described above, wherein adjusting the pH comprises adjusting with a buffer.

It is a further aspect of the present invention to provide the method as described above, further comprising forming the sample solution by diluting a sample comprising albumin 50- to 100000-fold with a buffer.

It is a further aspect of the present invention to provide the method as described above, further comprising incubating the sample solution for up to 100 hr, and performing said forming step prior to step B).

It is a further aspect of the present invention to provide the method as described above, wherein the buffer is selected from the group consisting phosphate buffer, Tris-HCl buffer, borate buffer, citrate buffer, acetate buffer, carbonate buffer, HEPES buffer, succinate buffer, and combinations thereof.

It is a further aspect of the present invention to provide the method as described above, wherein the sample solution is selected from the group consisting of blood and plasma, and is taken from a test subject.

It is a further aspect of the present invention to provide the method as described above, wherein incubating comprises incubating at an incubation temperature of 4-60° C.

It is a further aspect of the present invention to provide the method as described above, comprising subjecting the sample solution to ultrafiltration before step B).

It is a further aspect of the present invention to provide the method as described above, comprising subjecting the sample solution to purification by chromatography before step B).

It is a further aspect of the present invention to provide the method as described above, wherein the chromatography is selected from the group consisting of high performance liquid chromatography, reversed phase chromatography, normal phase chromatography, affinity chromatography, ion exchange chromatography, gel filtration chromatography, hydrophobic chromatography, and combinations thereof.

It is a further aspect of the present invention to provide the method as described above, wherein the mass spectrometry is performed using an apparatus selected from the group consisting of an electrospray ionization time-of-flight mass spectrometer, a quadrupole mass spectrometer, an ion trap mass spectrometer, a Fourier transform ion cyclotron mass spectrometer, a matrix-assisted laser desorption-ionization time-of-flight mass spectrometer, a magnetic sector-type mass spectrometer, a tandem quadrupole mass spectrometer, and combinations thereof.

It is a further aspect of the present invention to provide the method as described above, comprising determining the amount of reduced albumin and oxidized albumin, and/or the ratio of reduced albumin to oxidized albumin in the sample solution.

It is a further aspect of the present invention to provide the method as described above, wherein the sample solution is taken from a test subject who has, or is suspected of having, a condition selected from the group consisting of a hepatic disease, a renal disease, diabetes, rheumatism, encephalopathy, fatigue, aging, oxidative stress, a cardiac disease, a lung disease, and combinations thereof.

It is a further aspect of the present invention to provide a method of analyzing blood or plasma taken from a test subject who has, or is suspected of having, a condition selected from the group consisting of a hepatic disease, a renal disease, diabetes, rheumatism, encephalopathy, fatigue, aging, oxidative stress, a cardiac disease, a lung disease, and combinations thereof, the method comprising analyzing the amount of reduced albumin and oxidized albumin, and/or the ratio of reduced albumin to oxidized albumin in blood or plasma taken from the test subject according to the method as described above.

It is a further aspect of the present invention to provide a method of screening a test substance, the method comprising A) measuring the amount of reduced albumin and oxidized albumin, and/or the ratio of reduced albumin to oxidized albumin in sample solutions from a test subject both with and without administration of a test substance, said measuring comprising analyzing as described above, B) comparing the amount and/or the ratio obtained with administration of the test substance and the amount and/or ratio obtained without administration of the test substance, and C) selecting a sample having a greater amount and/or ratio of reduced albumin with administration of the test substance as compared to non-administration of the test substance.

It is a further aspect of the present invention to provide the method as described above, wherein the test substance is an antioxidant.

It is a further aspect of the present invention to provide a method of producing a reduced or oxidized albumin standard for quantitative analysis of albumin, the method comprising A) removing low-molecular compounds by purification, and B) adjusting the pH of the standard.

It is a further aspect of the present invention to provide the method as described above, wherein the quantitative analysis of albumin is a determination of the amount or ratio of reduced albumin and oxidized albumin in a test sample.

It is a further aspect of the present invention to provide the method as described above, comprising adjusting the pH to 4-9.

It is a further aspect of the present invention to provide the method as described above, wherein adjusting the pH comprises adjusting using a buffer selected from the group consisting of phosphate buffer, Tris-HCl buffer, borate buffer, citrate buffer, acetate buffer, carbonate buffer, HEPES buffer, succinate buffer, and combinations thereof.

It is a further aspect of the present invention to provide the method as described above, wherein purifying comprises ultrafiltration or chromatography.

It is a further aspect of the present invention to provide a method of producing an oxidized albumin standard for quantitative analysis of albumin, the method comprising A) adding cysteine or homocysteine to the standard, B) removing low-molecular compounds by ultrafiltration or purification by chromatography, C) adjusting the pH of the standard.

It is a further aspect of the present invention to provide the method as described above, wherein the quantitative analysis of albumin is a determination of the amount or ratio of reduced albumin and oxidized albumin in a test sample.

It is a further aspect of the present invention to provide the method as described above, wherein adjusting the pH comprises adjusting to pH 4-9.

It is a further aspect of the present invention to provide the method as described above, wherein adjusting the pH comprise adjusting using a buffer selected from the group consisting of phosphate buffer, Tris-HCl buffer, borate buffer, citrate buffer, acetate buffer, carbonate buffer, HEPES buffer, succinate buffer, and combinations thereof.

It is a further aspect of the present invention to provide a reduced or oxidized albumin standard for quantitative analysis of albumin, which is obtained by the method as described above.

It is a further aspect of the present invention to provide an oxidized albumin standard for quantitative analysis of albumin, which is obtained by the method as described above.

It is a further aspect of the present invention to provide a standard for the measurement of the ratio of reduced albumin to oxidized albumin in a sample, comprising albumin wherein the free cysteine residue at the 34th position from the N-terminus in the amino acid sequence of the albumin is not modified, and albumin wherein a thiol compound other than albumin is bonded to the free cysteine residue at the 34th position from the N-terminus in the amino acid sequence of the albumin via a disulfide bond.

It is a further aspect of the present invention to provide the standard as described above, wherein the thiol compound is selected from the group consisting of cysteine, homocysteine, and glutathione.

It is a further aspect of the present invention to provide the standard as described above, which is produced using albumin prepared from the blood.

It is a further aspect of the present invention to provide the standard as described above, which is produced using albumin prepared by recombinant DNA technology.

It is a further aspect of the present invention to provide the standard as described above, wherein the pH is adjusted to 4-9.

It is a further aspect of the present invention to provide the standard as described above, further comprising a solution dissolved in a buffer selected from the group consisting of phosphate buffer, Tris-HCl buffer, borate buffer, citrate buffer, acetate buffer, carbonate buffer, HEPES buffer, succinate buffer, and combinations thereof.

It is a further aspect of the present invention to provide the standard as described above, which is free of a thiol compound other than albumin, wherein the free cysteine residue at the 34th position from the N-terminus in the amino acid sequence of albumin is not modified.

with the plasma of a diabetic model mouse after freeze-thawing, incubated at 37° C. for 2 hr, with the plasma of a diabetic model mouse after freeze-thawing and no subsequent incubation, with the plasma of a normal model mouse after freeze-thawing, incubated at 37° C. for 2 hr, and with the plasma of a normal model mouse after freeze-thawing and no subsequent incubation.

Alb-Cys refers to the peak of a cysteine-added oxidized albumin, Alb-GSH refers to the peak of glutathione-added oxidized albumin, and Alb-glc refers to the peak of glycated albumin.

Figure 9:
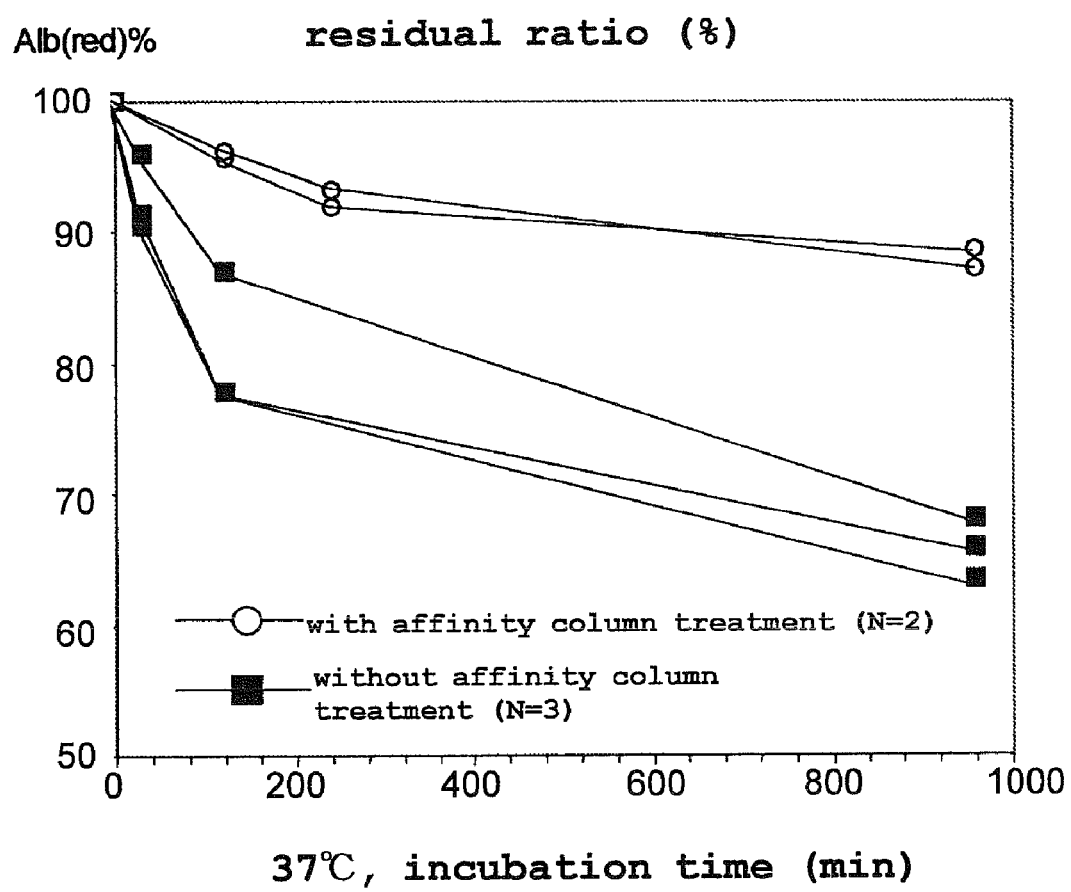

FIG. 9 is a graph showing the results of Example 5.

Figure 10:
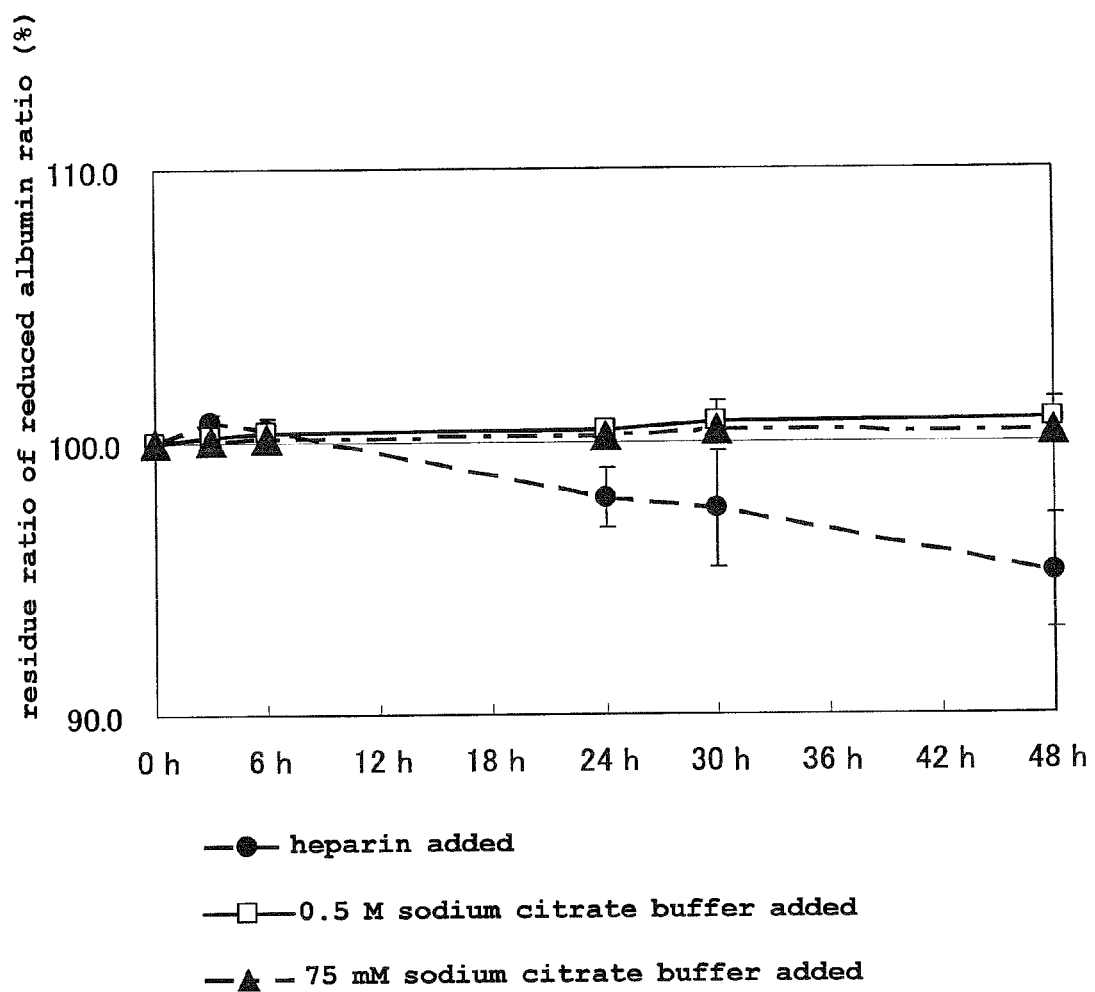

FIG. 10 is a graph showing the results of Example 6.

Figure 11:
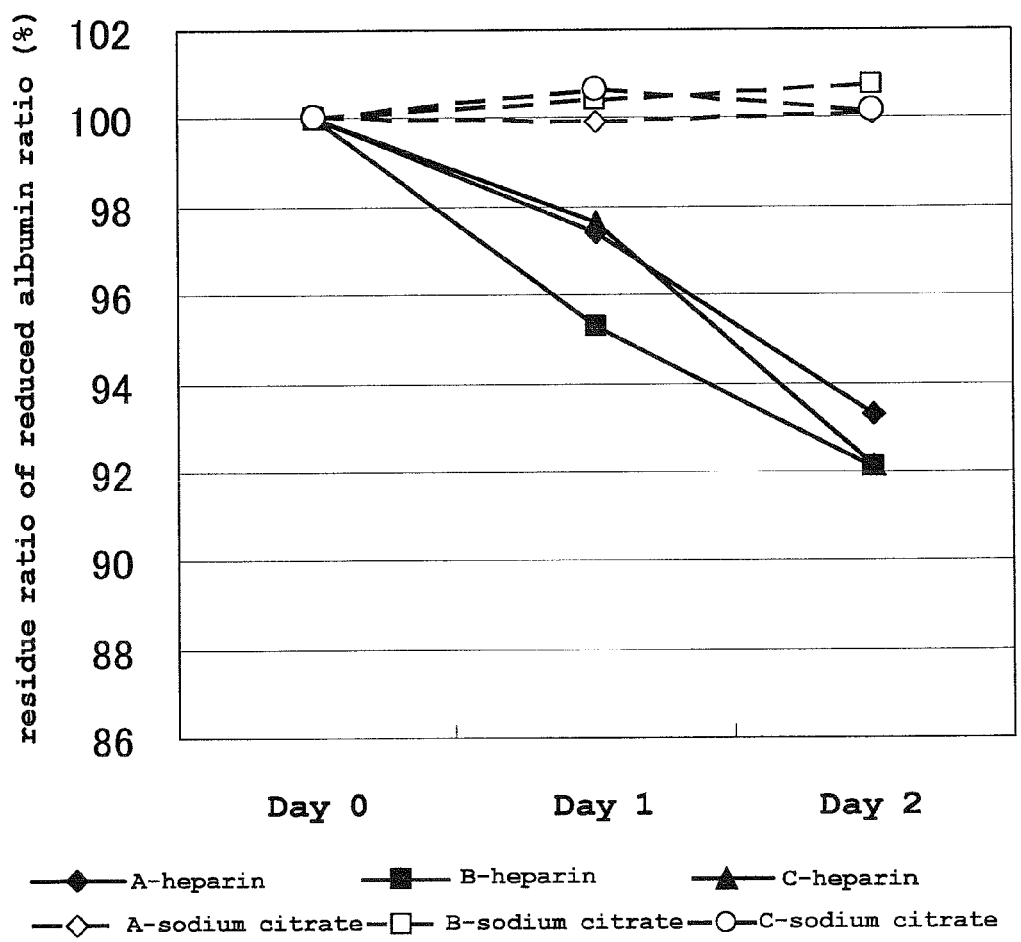

FIG. 11 is a graph showing the results of Example 8.

Figure 12:
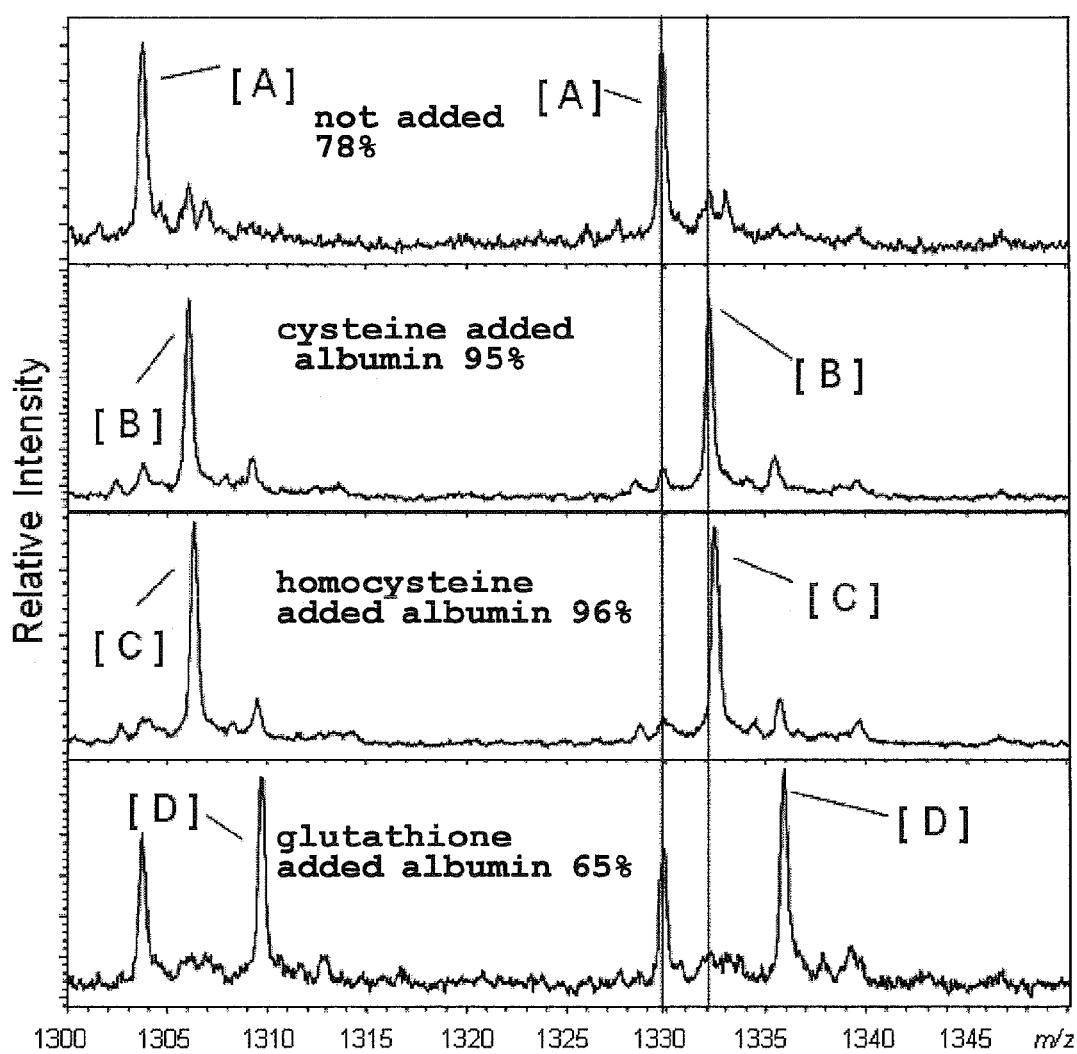

FIG. 12 is a chart showing the results of HPLC-ESI-TOFMS in Example 9.

DESCRIPTION OF THE PREFERRED EMBODIMENTS

Albumin can be analyzed in a more stable and accurate manner in a sample solution by the method described herein. In this method, the pH of the sample solution is adjusted to be between pH 4-9 before subjecting the sample solution to mass spectrometry or liquid chromatography. More preferably, the sample solution is adjusted to pH 5.8-6.2. When the pH of the sample solution is less than 4 or more than 9, it is difficult to analyze albumin while maintaining stability, because oxidization of reduced albumin to oxidized albumin occurs even during the preparation of the sample solution.

The pH of the sample solution may be adjusted by dissolution in a buffer, addition of a weak acidic solution or weak basic solution, and the like.

Of these, adjusting the pH with a buffer is preferable since this adjustment step can be performed simultaneously with the dilution step of the described method. Examples of the chosen buffer may include conventional buffers such as phosphate buffer, Tris-HCl buffer, borate buffer, citrate buffer, acetate buffer, carbonate buffer, HEPES hydrochloride buffer, succinate buffer, and the like. Particularly preferred are citrate buffer and phosphate buffer.

The present invention is particularly suitable for the analysis of albumin in blood or a plasma sample taken from a test subject.

To monitor the balance between oxidation and reduction in the sample, it is preferable to incubate the blood or plasma sample for up to 100 hr, preferably between 2-12 hr, prior to adjusting the pH or diluting the solution, or prior to the ultrafiltration or chromatography treatment when such is applied. This incubation period promotes the oxidation of reduced albumin, and further clarifies the difference between the amount of reduced albumin and oxidized albumin in the sample. In this way, more convenient monitoring of the balance between oxidation and reduction in the sample is possible.

The incubation temperature is, for example, 4-60° C., preferably 25-40° C.

The solution sample may be obtained by diluting a sample 50- to 100000-fold with a dilution solvent. When the dilution rate is smaller than 50-fold, reduced albumin is rapidly converted to oxidized albumin. This is because the frequency of contact between low-molecular compounds and reduced albumin is high. In this case, moreover, when a buffer is used as the diluent, the ability of the buffer to buffer the pH is inhibited. Alternatively, when the dilution rate is greater than 100000-fold, the albumin concentration may fall below the detection limit of the apparatus. In this case, however, the injection amount of the sample may be increased to compensate for the greater dilution ratio, and allow for detection.

Examples of the dilution solvent include various buffers, water, acetonitrile, methanol, formic acid solution, and the like. As mentioned above, a buffer is preferable since the pH can be adjusted during the same step. Examples of the buffer include those mentioned for adjusting the pH. Of those, phosphate buffer is particularly preferable.

To suppress the oxidation of albumin, it is preferable to remove low-molecular compounds that may be present in the sample.

Low-molecular compounds may be removed, for example, by ultrafiltration, or purification by chromatography such as high performance liquid chromatography, reversed phase chromatography, normal phase chromatography, affinity chromatography, ion exchange chromatography, gel filtration chromatography, hydrophobic chromatography, and the like.

Of these, purification by affinity chromatography using an affinity column having high albumin adsorption capacity is preferable. A sample is applied to an affinity column to allow for absorption of albumin in the sample to the column resin. The inside of the column is then washed with phosphate buffer to remove the low-molecular weight compounds while leaving the albumin adsorbed on the column. After the wash, a phosphate buffer having a high salt concentration is applied to the column to elute the albumin. As a result, albumin is released from the resin, and a sample which is free of low-molecular compounds is obtained.

Examples of the low-molecular compounds as mentioned above include compounds having a molecular weight of not more than 2,000, preferably not more than 1,000, and more preferably not more than 500. Examples include amino acids, organic acids, saccharides, fatty acids, lipids, nucleic acids, nucleotides, nucleosides, metal ions, steroid compounds, peptides, and the like. More specifically, cysteine, cystine, homocysteine, homocystine, reduced glutathione, and oxidized glutathione can be mentioned.

When ultrafiltration is performed, the pore size of the filtration filter is generally for a molecular weight of 1000 Da-60000 Da, and preferably, a pore size of 10000 Da-30000 Da.

While low-molecular compounds are generally removed immediately before mass spectrometry or liquid chromatography, it is also possible to remove them in advance using a gel-inclusion collection instrument, or a pH adjustment dilution solvent-inclusion collection instrument, during collection of a sample such as blood, plasma, and the like. For example, since a blood collection tube of Biopool for a plasminogen activator assay (U.S. Pat. No. 5,175,087) uses a citrate buffer, the use thereof allows for pH adjustment during the collection of the blood sample and stabilization of albumin.

In addition, it is preferable to perform purification by chromatography or LC-MS before mass spectrometry, thereby to prevent the presence of a peak due to contaminants other than albumin.

Examples of the type of chromatography which may be used for purification include those exemplified for the removal of low-molecular compounds. Of these, reversed phase high performance liquid chromatography that can be easily connected to mass spectrometry as LC-MS is preferable.

Reduced albumin in the blood or plasma is highly unstable. Therefore, when a sample solution is blood, such as whole blood, cryotreatment is generally not preferable, because the freezing causes destruction of red blood cells and the hemoglobin in the red blood cells affects the measurement. Thus, it is advantageous to adjust the pH or dilute the sample immediately after blood collection, preferably by ultrafiltration, and apply the blood to the measurement apparatus. Use of an adjustable pH collection tube, for example, a blood collection tube containing a dilution solvent to adjust the pH, and the like is more preferable. When the sample solution is plasma, the plasma may be separated after blood collection, rapidly frozen using liquid nitrogen, and cryopreserved at −70° C. or lower.

The pH adjustment, dilution, ultrafiltration, and chromatography may be performed prior to cryopreservation of a plasma sample. Alternatively, they may be performed after thawing a cryopreserved plasma sample. It is also possible to treat the sample using a gel-inclusion collection utensil, or a pH adjustment dilution solvent-inclusion collection utensil, before cryopreservation or during collection of the blood. As a result, the sample can be stably stored for a long time even at higher storage temperatures.

Examples of the mass spectrometers which can be used for the described method include an electrospray ionization-time-of-flight mass spectrometer (ESI-TOFMS), a quadrupole mass spectrometer, an ion trap mass spectrometer, a Fourier transform ion cyclotron mass spectrometer, a matrix-assisted laser desorption/ionization-time-of-flight mass spectrometer (MALDI-TOFMS), a magnetic sector-type mass spectrometer, a tandem quadrupole mass spectrometer, and the like. Of these, ESI-TOFMS is preferable for its simplicity, high mass resolution capability, and high sensitivity.

The amount of reduced albumin and oxidized albumin, the ratio of reduced albumin to oxidized albumin, the presence or absence of glycated albumin, the identification of the presence of different types of oxidized albumin, and the like can be analyzed for a sample solution.

"Reduced albumin" indicates albumin wherein the free cysteine residue at the 34th position from the N-terminus is not modified.

"Oxidized albumin" indicates albumin wherein a thiol compound other than albumin is bonded to the free cysteine residue at the 34th position from the N-terminus via a disulfide bond.

By analyzing the amount of reduced albumin and oxidized albumin and/or the ratio of reduced albumin to oxidized albumin in blood or plasma taken from a test subject by the method described herein, one may determine whether or not the test subject is suffering from a hepatic disease, a renal disease, diabetes, rheumatism, encephalopathy, fatigue, aging, oxidative stress, a cardiac disease, and/or a lung disease.

Examples of the test subject from whom a blood or plasma sample can be collected include mammals, for example, a mouse, rat, hamster, rabbit, cat, dog, bovine, sheep, monkey, human, and the like.

The following conditions are known to produce oxidative stress: hepatic disease, renal disease, diabetes, rheumatism, encephalopathy, fatigue, aging, oxidative stress, cardiac disease, lung disease, and the like. These conditions are also known to upset the balance between oxidation and reduction in the test subject. That is, when a test subject has one of more of these conditions, the amount of oxidized albumin relative to the total amount of oxidized albumin and reduced albumin in the test subject increases. Therefore, by analyzing the amount of oxidized albumin, regardless of whether or not the test subject has been diagnosed with one or more of these diseases or conditions, such a diagnosis can be determined.

Examples of the hepatic disease include hepatitis C, hepatitis B, cirrhosis, hepatic encephalopathy, primary biliary cirrhosis, liver cancer, and the like.

Examples of the renal disease include renal failure, glomerulonephritis, nephrosis syndrome, pyelonephritis, and gout kidney.

Examples of the encephalopathy include cerebral apoplexy, cerebral infarction, hepatic encephalopathy, subarachnoid hemorrhage, and the like.

Examples of the cardiac disease include angina pectoris, myocardial infarction, arrhythmia, congenital cardiac disease, and the like.

Examples of the lung disease include pneumonia, emphysema, asthma, bronchitis, and the like.

Using the albumin analysis method described herein, a test substance can also be screened for the amount of reduced albumin and oxidized albumin and/or the ratio of reduced albumin to oxidized albumin, and used as an index. Using the albumin analysis method described herein, this screening for a test substance includes the following steps: 1) determination of the amount of reduced albumin and oxidized albumin and/or the ratio of reduced albumin to oxidized albumin in a subject with or without administration of a sample substance, 2) comparing the amount and/or the ratio in the subject who took the test substance to the amount and/or ratio in the subject who did not take the test substance, and 3) selecting the test subject having a greater amount and/or ratio of reduced albumin with administration of test substance as compared to non-administration thereof.

Examples of the test substance include various drugs and health materials such as antioxidants, albumin-binding substances, etc. As used herein, health materials include food materials which maintain or improve health, and foods containing the same. Examples of drugs include prophylactic or therapeutic drugs for hepatic disease, renal disease (particularly nephrosis syndrome), diabetes, cardiac disease and aging, and the like. In addition, examples of the health materials include nutrient sources/supplements such as antioxidants, vitamins, amino acids, minerals, carbohydrates, fatty acids, enzymes, etc.

A test substance having more than about 0.1 mg/mL of reduced albumin, preferably more than about 0.2 mg/mL, may be a candidate for a useful drug or health material. When measuring the ratio, a test substance having a greater ratio of reduced albumin to the total albumin of not less than 2%, preferably not less than 3%, more preferably not less than 5%, may be a candidate for a useful drug or health material.

Pre-treating a sample solution used in the albumin analysis method described herein can markedly suppress the oxidation reaction of albumin in the blood or plasma. Such pre-treatment includes by adjusting the pH and preferably, by dilution and/or removal of low-molecular compounds by ultrafiltration and chromatography. As a result, the ability to preserve, store, and transport the sample becomes markedly simple. Moreover, when samples are pre-treated as described herein prior to the albumin analysis method described herein, the effect of the natural oxidation of albumin on the results is suppressed as much as possible as compared to when using a conventional HPLC method, and stable Alb(red) % values are obtained. Furthermore, use of the albumin analysis method described herein allows for accurate albumin quantification, unlike the conventional serum albumin quantification methods.

Mass spectrometry or liquid chromatography may be used as an analysis method. Particularly, LC-MS is more effective as a detection method in terms of sensitivity and selectivity. When mass spectrometry is used, detection and quantitation are possible with as little as about a 0.2 nL sample, as compared to 10 μL that are required for conventional HPLC methods. In addition, since mass spectrometry is generally highly sensitive as compared to liquid chromatography, the sample solution may be sufficiently diluted to facilitate adjusting the pH to fall within a particular range and permit a higher dilution ratio, and the like, thereby reducing the frequency of contact of the Alb(red) with reactive compounds in the sample solution. Herein, the selectivity refers to that of Alb(red) and Alb(ox). When mass spectrometry is used, since selectivity is higher than that of liquid chromatography, baseline separation can be achieved for Alb(red) and Alb(ox). Furthermore, when mass spectrometry is used, since the detection is based on m/z values, the structure information can be obtained as necessary from the peak on the mass spectrum, in addition to the Alb(red) % values.

Albumin is highly unstable and, during incubation, oxidized albumin increases due to natural oxidation. In fact, when sample solutions obtained by incubating plasma for a given period of time, adjusting the pH, diluting the sample solution, and then performing mass spectrometry or liquid chromatography, the rate of change of Alb(red) % varies depending on the samples. That is, albumin acts like a probe that indicates the redox state of plasma.

One of the approaches to drug discovery is to search for candidate drugs using large-scale combinatorial synthesis. The methods described herein allow for convenient and rapid screening of a drug effect because it is highly convenient, permits rapid measurement of 35 min per sample, and enables automation using an auto injector since the sample does not need to be analyzed immediately after freeze-thawing.

The methods described herein further provide for preparation of a reduced or oxidized albumin standard, which permits accuracy and control of the albumin quantitative analysis, including removing low-molecular compounds by purification and adjusting the pH.

In the methods described herein, the albumin standard refers to an albumin solution having a constant and stable ratio of reduced albumin to oxidized albumin. Of such albumin standards, one containing more reduced albumin than oxidized albumin (preferably more than 50%, more preferably not less than 70%, of the total albumin is reduced albumin) in a solution is referred to as a reduced albumin standard, and one containing more oxidized albumin than reduced albumin (preferably more than 50%, more preferably not less than 70%, of the total of albumin in is oxidized albumin) in a solution is referred to as an oxidized albumin standard.

The methods described herein also provide a method for producing an oxidized albumin standard for accurate and controlled quantitative analysis of albumin, which includes adding cysteine, homocysteine or glutathione, removing low-molecular compounds by ultrafiltration or purification by chromatography, and adjusting the pH.

Stable albumin standards obtained by these preparation methods are also encompassed in the scope of the present invention. Particularly, the above-mentioned albumin standard sample is suitable for controlling accuracy of measurement of Alb(red)

The adjustment of pH and removal of low-molecular compounds may be accomplished as mentioned above.

The present invention also provides a standard for the measurement of the ratio of reduced albumin to oxidized albumin in a test sample. The standard may be albumin wherein a free cysteine residue at the 34th position from the N-terminus in the amino acid sequence of albumin is not modified (reduced albumin), and albumin wherein a thiol compound other than albumin is bonded to a free cysteine residue at the 34th position from the N-terminus in the amino acid sequence of albumin via a disulfide bond. Here, specific examples of the thiol compound other than albumin include cysteine, homocysteine, and glutathione.

The above-mentioned standard is preferably prepared from blood, or using albumin prepared by recombinant DNA technology.

The method for preparing albumin from blood is not particularly limited, and a method generally used in the field can be appropriately used. For example, subjecting a collected blood sample to chromatography, and separating or purifying the albumin can be mentioned. In this case, the albumin (reduced albumin+oxidized albumin) concentration of a standard solution is preferably 0.1-50 mg/ml.

The method of preparing albumin by recombinant DNA technology is not particularly limited, and a method which is generally used in the field can be appropriately used. A recombinant DNA human serum albumin produced using a yeast expression system has been reported (Fleer R. et al, Biotechnology (NY). 1991 October; 9(10): 968-75), and for example, the method described in this reference can be used.

The pH of the above-mentioned standard is preferably adjusted to pH 4-9 to ensure the stability of the reduced and oxidized albumin.

A solution obtained by dissolving the above-mentioned standard in a buffer such as phosphate buffer, Tris-HCl buffer, borate buffer, citrate buffer, acetate buffer, carbonate buffer, HEPES buffer and succinate buffer is preferable.

Furthermore, the above-mentioned standard is preferably free of a thiol compound other than reduced albumin.

According to the present invention, since the amount and/or the ratio of reduced albumin and oxidized albumin in a sample solution can be conveniently and accurately measured, the balance between oxidation and reduction in a test subject can be monitored. As a result, whether or not a test subject has oxidative stress, or hepatic disease, renal disease, diabetes, rheumatism, encephalopathy, fatigue, aging, cardiac disease, lung disease and the like, in which oxidized albumin increases, can be determined. According to the present invention, moreover, a drug for the prophylaxis or treatment of hepatic disease, renal disease, diabetes, rheumatism, encephalopathy, fatigue, aging, oxidative stress, cardiac disease, lung disease and the like can be screened for. Furthermore, an antioxidant to be a health material can also be screened for. Moreover, oxidative stress can be monitored during drug administration, and effective drugs can be screened for.

The present invention is explained in detail in the following by referring to Examples, which are not to be construed as limitative.

EXAMPLE 1

A rat plasma sample was prepared as follows. The rat was anesthetized with diethyl ether by inhalation, and the blood was collected. Plasma was obtained by immediately centrifuging the collected blood. Then, the plasma fraction was placed in another test tube, frozen with liquid nitrogen, and cryopreserved at −80° C.

This plasma sample was thawed in an ice bath, diluted 100-fold with 50 mM $NaH_2PO_4/Na_2HPO_4$ (pH 6.0), and analyzed by HPLC-ESI-TOFMS.

A human plasma sample was prepared as follows. Blood was collected from a human test subject into a vacuum blood collection tube containing heparin, and transferred to a polypropylene tube for centrifugation at 4° C. and 3000 rpm for 20 min. The supernatant fraction was used as the plasma component.

HPLC-ESI-TOFMS was performed using a system connecting a high performance liquid chromatography apparatus (HPLC: Ultimate Plus Capillary/Nano LC System, Dionex Corporation, USA) and an electrospray-ionization time-of-flight mass spectrometer (ESI-TOFMS: microTOF™, BRUKER Daltonics Inc., USA). The HPLC apparatus consisted of three modules: a micro auto injector (FAMOS), a micro flow pump of split system (Ultimate), and a pump mounted switching valve (Switchos).

The albumin in the sample was separated and concentrated using a trap column (MonoCap concentration column: GL Science Inc., inner diameter 0.2 mm, length 150 mm) and a separation column (MonoCap for Fast-flow: inner diameter 0.2 mm, length 50 mm).

The eluents for HPLC were solution (A) [acetonitrile/water (Milli-Q)(25:75 v/v, 1 L) mixture added with formic acid (1 mL)], and solution (B) [acetonitrile/water (Milli-Q)(90:10 v/v, 1 L) containing formic acid (1 mL)]. The sample tray of the auto injector was set to 4° C., and the sample vials were continuously cooled.

The trap column was equilibrated by applying solution (A) at a flow rate of 0.05 mL/min, and the separation column was equilibrated by applying solution (B) at a flow rate of 15 µL/min. The pump set flow rate was 0.125 mL/min, and the substantial flow rate was 15 µL/min by split flow path.

After dilution and filtration, the above-mentioned solution was placed in a vial, set on a sample tray and the measurement was started. The volume of the sample injection was set to 2 µL, and solution (A) was applied at 0.05 mL/min from the Swichos module from 0 min to 10 min from the start of the measurement, during which time salt and contaminants in the sample passed through the trap column and albumin was adsorbed by the trap column, achieving desalting and concentration. From 10 min to 15 min from the start of the measurement, the flow path was changed by the switching valve to form a flow path connecting the trap column and the separation column. At this time, by applying solution (B) from the Ultimate module at a flow rate of 15 µL/min, albumin adsorbed on the trap column was transferred to and retained in the separation column. From 15 min to 35 min from the start of the measurement, the flow path was changed again to form separate flow paths for the trap column and the separation column, during which time solution (B) was applied from the Ultimate module at a flow rate of 15 µL/min, wherein other contaminant components containing albumin were crudely separated. Alternatively, from 15 min to 25 min from the start of the measurement, solution (B) was applied from the Switchos module at a flow rate of 0.07 µL/min, whereby residual substances were retained in the trap column and eluted. From 25 min to 35 min from the start of the measurement, solution (A) was applied from the Switchos module at a flow rate of 0.07 µL/min, whereby the trap column was initiated with solution (A).

Albumin eluted from the separation column was ionized at an electrospray ion source, the interface between high performance liquid chromatography and mass spectrometer, and detected by the mass spectrometer. All mass spectra were conducted with optimized ionization and ion detection parameters. The detection mass range of the mass spectrometer was set to m/z 50-3000, and the multi-valent albumin charged with a positive ion was detected. The ionization parameter conditions were the following: End Plate Offset: −500 V, Capillary: −5000 V, Neblizer Gas: 0.4 Bar, Dry Gas: 5.0 L/min, Dry Temp: 200° C. The software to control mass spectrometer: the ionized albumin was detected by microTOF Control. The optimized conditions were: Capillary Exit: 150 to 250 V, Skimmer 1:50 to 100V, Hexapole 1:24 to 36V, Skimmer 2:25 to 35V, Hexapole 2:18 to 24V, Hexapole RF: 500 to 800V, Transfer Time: 30 to 50 µs, Pre Puls Storage: 20 to 40 µs, Lens 1 Storage: 30 to 60V, Lens 1 Extraction: 18 to 24V, Lens 2: −15 to +15V, Lens 3: −70 to −10V, Lens 4: −15 to +15V, Lens 5: −60 to +20V, Detector: 1400 to 1600V, Rolling Average: 3, Summation: 20000, Pulser Push/Pull: 380 to 400V, Corrector Fill: 40 to 50V, Corrector Extract: 800 to 1000V, Flight Tube: 9000V, Reflector: 1300V and TOF Detector: 1800 to 2000V.

Figure 1:
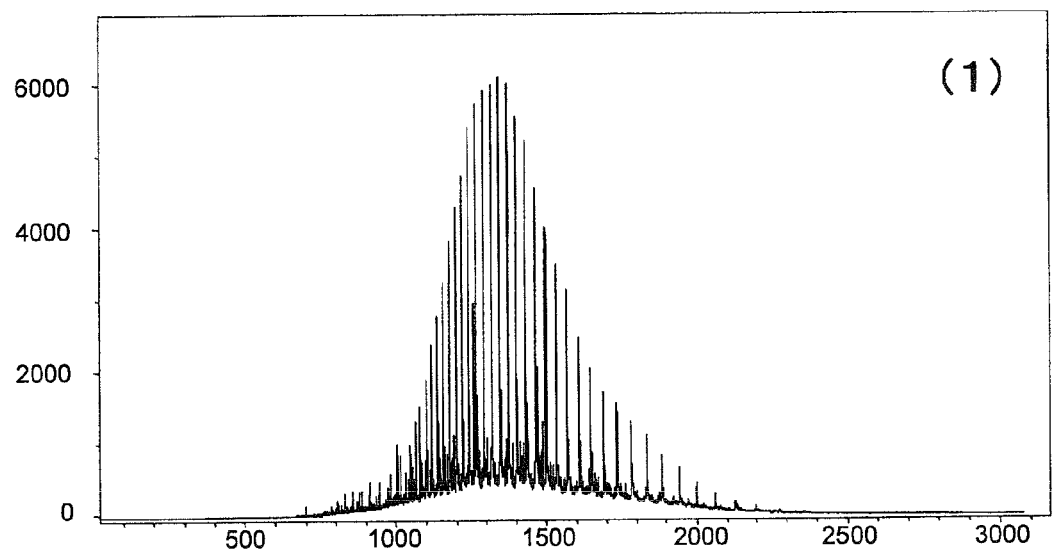
FIG. 1 shows the method for calculating the Alb(red) % value in Example 1.
Figure 1:
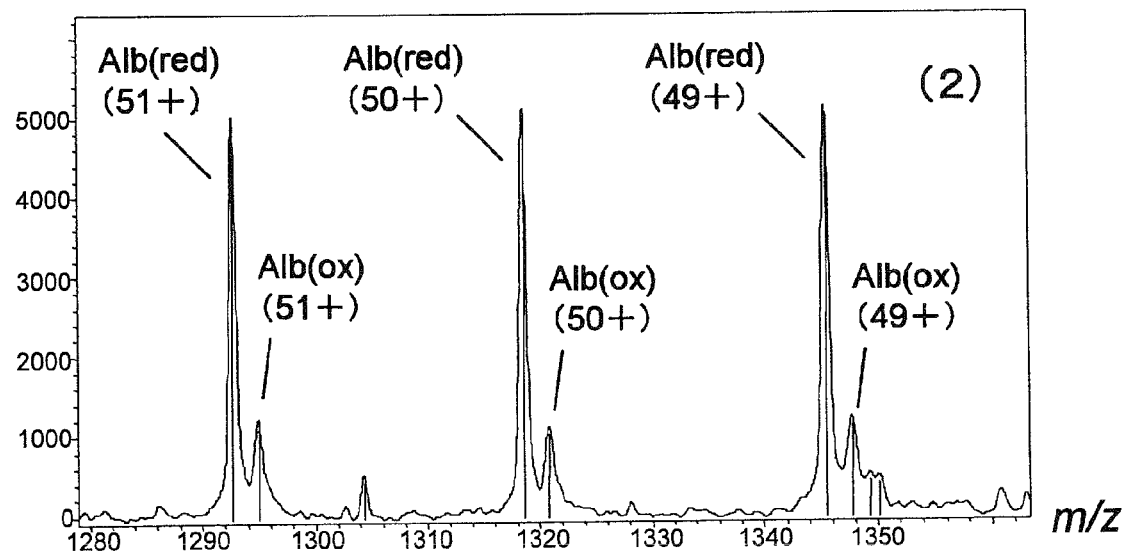

The mass spectrometer data analysis software microTOF Data analysis was used to analyze the data. The albumin ionized by the electrospray method formed multiply-charged ions, which were detected as plural peaks (FIG. 1(1)). For the mass spectrum, after a smoothing treatment (Gauss algorithm: m/z width=0.1, Cycle=1) and a baseline treatment, peaks of the same charge were determined by Deconvolution function. Two peaks showing the same charge were detected; a smaller m/z was assumed to be Alb(red), and a higher m/z was assumed to be Alb(ox) (FIG. 1(2)). The peaks detected within the range of m/z 1220 to 1410 were derived from multiply charged albumin (46+to 53+). From the peak intensity (height), Alb(red) %={Alb(red) peak intensity (height)/ (Alb(red) peak intensity (height)+Alb(ox) peak intensity (height))}×100 was determined for each valence and the average value was calculated.

Since the proportion of Alb(red) in the sample decreases due to a natural oxidation reaction, the Alb(red) % value tends to decrease with time. Therefore, the plasma sample was diluted 100-fold and filtered with a buffer to control the pH of the sample.

Figure 2:
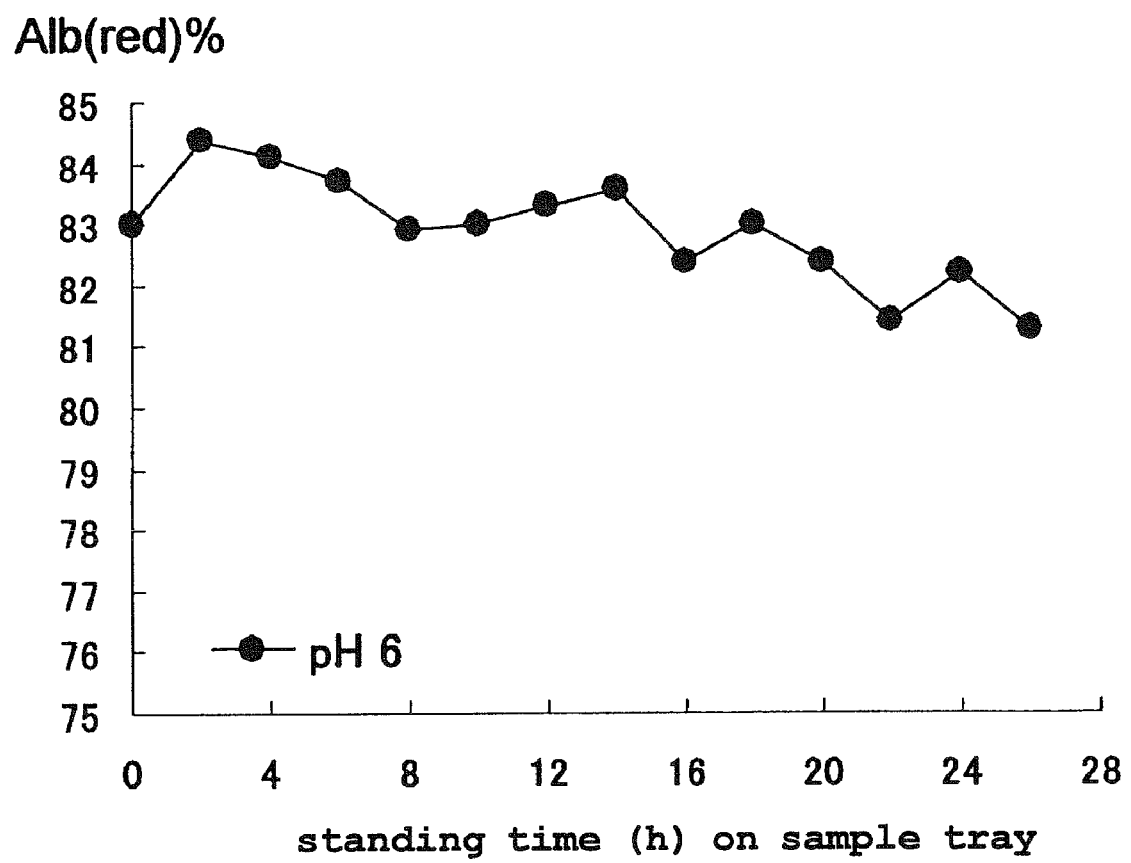
FIG. 2 is a graph showing the time course of the Alb(red) % value when the rat-derived sample solution was adjusted to pH 6 (Example 1).

When 50 mM phosphate buffer (pH 6.0) was used as the dilution solution for the rat plasma, a tendency toward a decrease in the Alb(red) % value was observed, but a stable Alb(red) % value was obtained at 24 hr after the treatment (FIG. 2).

Figure 3:
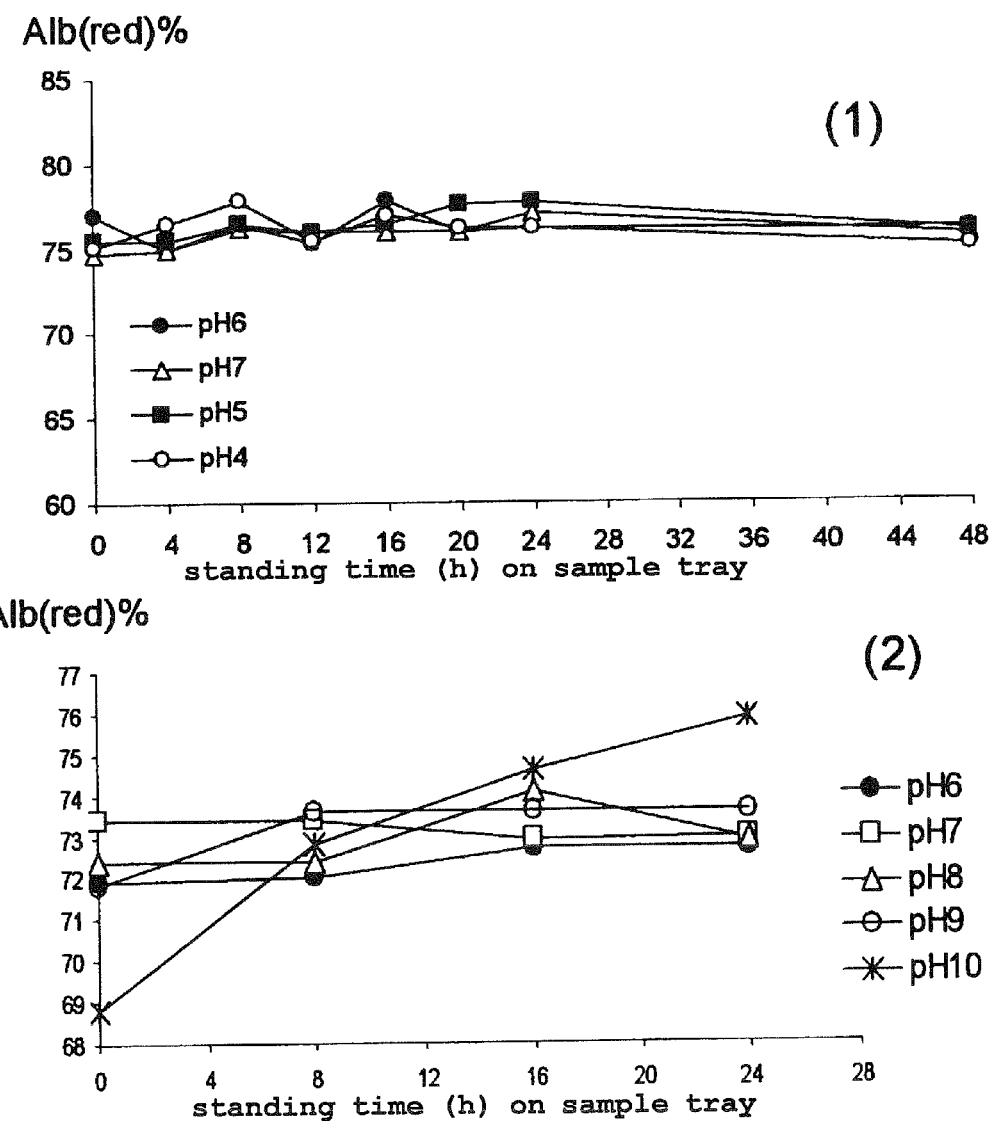
FIG. 3 is a graph showing the time course of the Alb(red) % value when the human-derived sample solutions were adjusted to various pHs (Example 1).

The stability test for Alb(red) was performed over a larger pH range for the human plasma. The dilution buffers were 50 mM acetate buffers (pH 3.0, pH 4.0 and pH 5.0), 50 mM phosphate buffers (pH 6.0, pH 7.0 and pH 8.0), and 0.1 M carbonate buffers (pH 9.0 and pH 10.0). The applicable range for an acidic pH was confirmed. As a result, an albumin-derived signal was not observed on the mass spectrum at pH 3.0, but at pH 4.0 to pH 7.0, a stable Alb(red) % value was obtained even after 48 hr from the start of standing on a sample tray (FIG. 3(1)). Similarly, the applicable range for an alkaline pH was confirmed. As a result, at pH 6.0 to pH 9.0, a stable Alb(red) % value was obtained even after 24 hr from the start of standing on a sample tray. At pH 10.0, however, a tendency toward an increase in the Alb(red) % value was confirmed with the lapse of standing time (FIG. 3(2)). As demonstrated, human plasma permits a stable measurement of Alb(red) % by using a dilution buffer at pH 4.0 to pH 9.0.

Since a sample solution treated by the method of the present invention shows stable Alb(red) % values even after standing on a sample tray for 24 hr, automation of the measurements using an auto injector is possible.

In addition, the effect of changing the dilution ratio on the Alb(red) % value was also studied. The dilution ratio was changed by 10-fold, 20-fold, 50-fold, or 100-fold with 50 mM phosphate buffer (pH 6.0).

Figure 4:
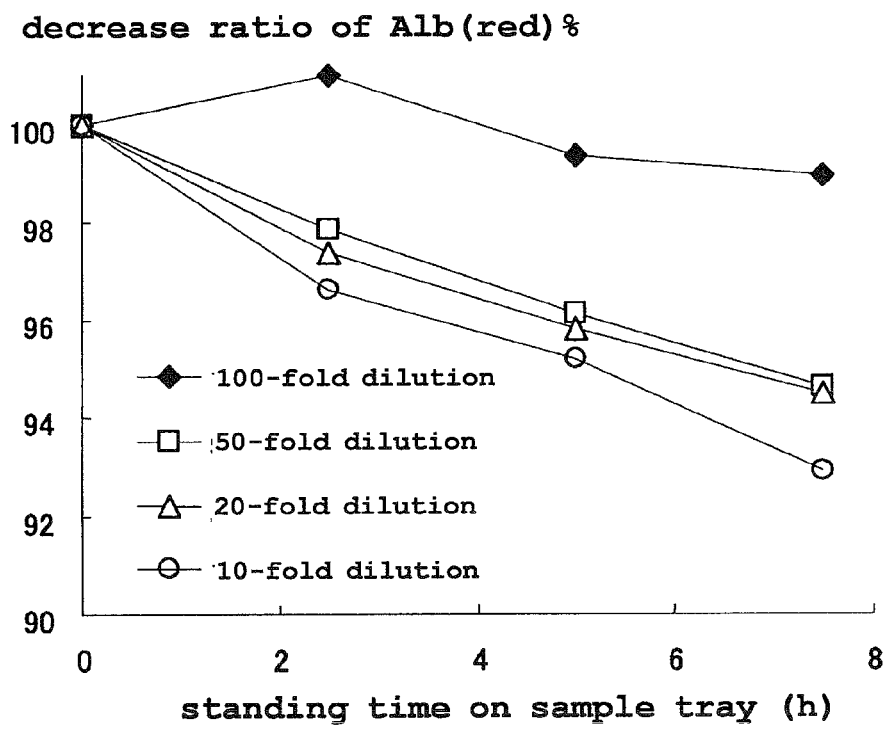
FIG. 4 is a graph showing the time course of the Alb(red) % value when the rat-derived sample solutions have various dilution rates (Example 1).

For the rat plasma, a 100-fold dilution ratio resulted in stable Alb(red) % values even 24 hr after the dilution/filtration treatment. At dilution ratios of 10-fold, 20-fold, and 50-fold, however, a decrease in the Alb(red) % value was observed after 2 hr standing on a sample tray, and the decrease grew with time (FIG. 4).

Figure 5:
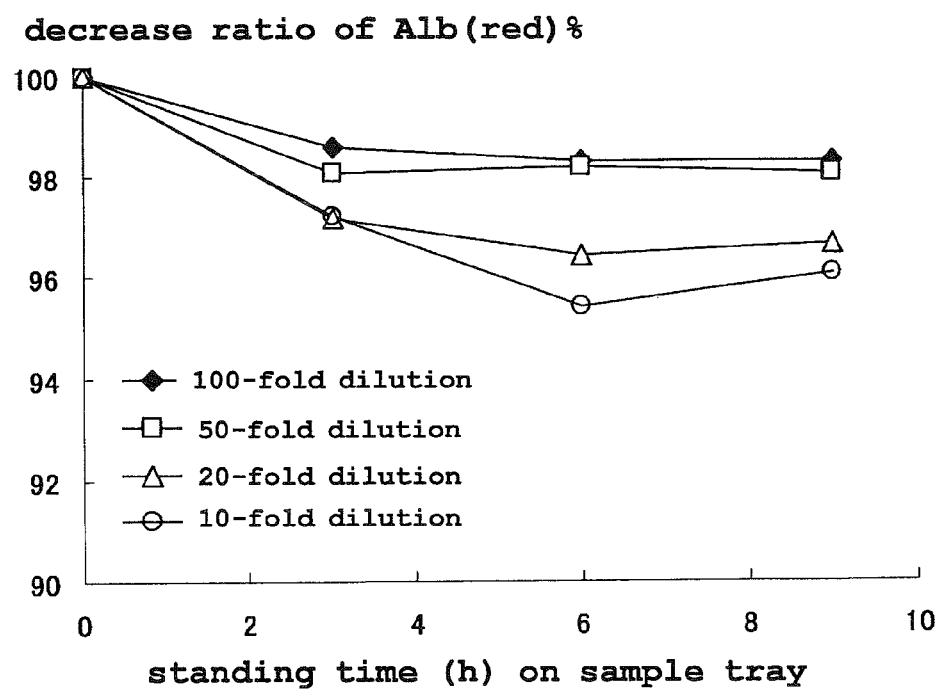
FIG. 5 is a graph showing the time course of the Alb(red) % value in the human-derived sample solutions at various dilution rates (Example 1).

For the human plasma, a 50-fold or 100-fold dilution ratio resulted in stable Alb(red) % values even 24 hr after the dilution/filtration treatment. At dilution ratios of 10-fold and 20-fold, however, a decrease in the Alb(red) % value was observed after 3 hr standing on a sample tray, and the value further decreased thereafter and reached an approximately constant value after 6 hr (FIG. 5).

EXAMPLE 2

Plasma samples of a hepatic disease model in rats were prepared by repetitive administration of carbon tetrachloride.

Hepatic disease-induced model rats were prepared by subcutaneously administering a mixture (1 mL/kg) of equivalent amounts of carbon tetrachloride ($CCl_4$) and olive oil to SD rats twice a week. Blood (1 mL) was collected under ether anesthesia from the subclavian vein monthly from the start of the $CCl_4$ administration. Simultaneously, blood was sampled from normal rats as a control group. The collected blood was immediately placed in an ice bath, and centrifuged within an hour to separate the plasma. The separated plasma was immediately frozen with liquid nitrogen and stored at −80° C. The samples were thawed before measurement and treated as described in the following (1) or (2). The Alb(red) % values of the plasma samples for both the normal rats and the hepatic disease model rats (22 weeks after the start of $CCl_4$ administration) were calculated.

(1) After freeze-thawing, the sample was immediately diluted 100-fold with 50 mM phosphate buffer (pH 6.0). Then, the solution was placed in a vial, set on an auto sampler set to temperature 4° C., and analyzed by HPLC-ESI-TOFMS.

(2) After freeze-thawing, plasma was incubated at 37° C. for 2 hr. After the incubation, a treatment similar to the treatment after freeze-thawing in (1) above was performed.

HPLC-ESI-TOFMS and calculation of Alb(red) % value were performed in the same manner as in Example 1.

Figure 6:
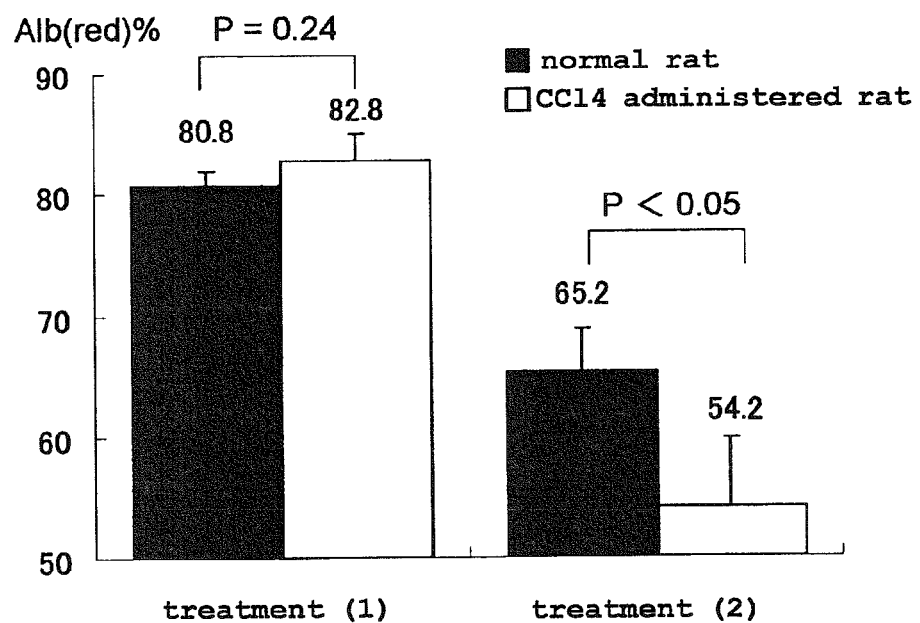
FIG. 6 is a graph showing the results of Example 2.

With treatment (1), the Alb(red) % value was 80.8±1.1 for the normal rats and 82.8±2.3 for the hepatic disease model rats. Alternatively, with treatment (2), the Alb(red) % value was 65.2±3.7 for the normal rats and 54.2±5.6 for the hepatic disease model rats (Table 1 and FIG. 6).

TABLE 1

Fluctuation of Alb(red) % values by change of pretreatment methods of normal rats and $CCl_4$ administrated rats

|  | treatment (1) | | treatment (2) | |
| --- | --- | --- | --- | --- |
|  | normal rats | $CCl_4$ administrated rats | normal rats | $CCl_4$ administrated rats |
| #1 | 82.0 | 82.3 | 63.7 | 49.6 |
| #2 | 79.8 | 80.8 | 69.4 | 52.7 |
| #3 | 80.5 | 85.3 | 62.6 | 60.4 |
| average | 80.8 | 82.8 | 65.2 | 54.2 |
| SD | 1.1 | 2.3 | 3.7 | 5.6 |
| RSD % | 1.4 | 2.8 | 5.6 | 10.3 |
| t-test | 0.240 | | 0.046 | |

With treatment (1), no significant difference was observed between the normal group and the hepatic disease model group. However, in treatment (2), a significant difference was observed between the normal rat group and the hepatic disease model rat group ($p<0.05$), and therefore, the pathology of hepatic disease can be conveniently monitored using Alb (red) %.

EXAMPLE 3

In the Examples presented above, Alb(red) % was analyzed using a liquid chromatography-mass spectrometer (LC-ESI-TOFMS). In the following Example, however, high performance liquid chromatography (HPLC) solely was used.

An AKTAexplorer 10S (GE Healthcare (formerly Amersham Biosciences AB), Sweden) system was used as the HPLC. 30 mM phosphate buffer (pH 6.85) containing 0.15 M sodium sulfate was used as an HPLC eluent at a flow rate of 0.8 mL/min. Shodex Asahipak GS-520 7E was used as the separation column. Measurement signals were monitored by UV detection (detection wavelength 280 nm).

Figure 7:
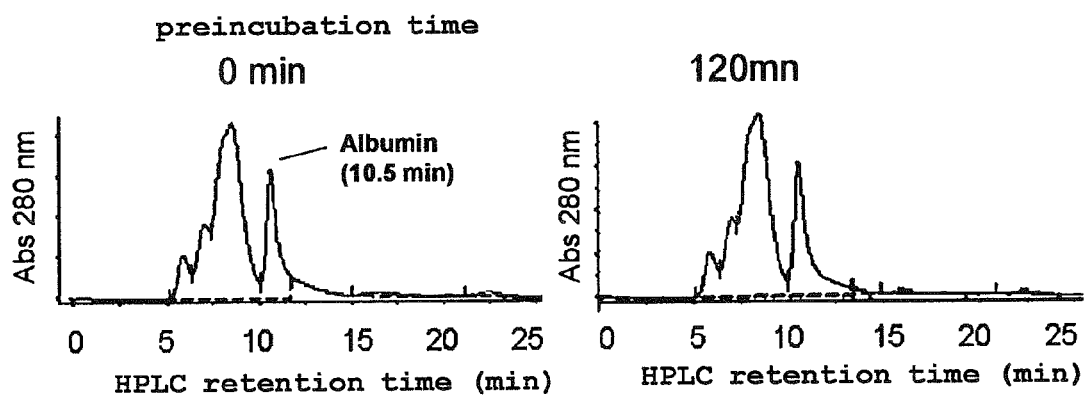
FIG. 7 is a chromatogram showing the results of Example 3.

A normal rat plasma sample cryopreserved at −80° C. was thawed in an ice bath, and diluted 5-fold with 50 mM phosphate buffer (pH 6.0). A 5-fold diluted sample which had been immediately applied to the HPLC apparatus, and a 5-fold diluted sample which had been preincubated for 2-hrs at room temperature were each analyzed. As a result, a peak corresponding to reduced albumin was observed on the chromatogram at approximately 10.5 min. Since no change was observed in the chromatogram pattern before and after the preincubation treatment, albumin in rat plasma was determined to be stable by virtue of the buffer at pH 6.0 (FIG. 7).

EXAMPLE 4

A KK-Ay mouse was modified by introducing the obesity gene Ay to induce a type 2 diabetic model that expresses obesity and hyperglycemia earlier and to a more severe extent than the KK mouse does. The KK-Ay mouse is a complicated model prepared by introducing the Ay gene into a KK mouse, and characteristically expresses obesity and hyperglycemia earlier (7-8-week-old) and to a more severe extent than the KK mouse does. Using a KK-Ay mouse (CLEA Japan, Inc.) as an inherited spontaneously diabetic model mouse, the Alb (red) % values of the plasma samples were measured. Blood collected from a normal mouse and a diabetic model mouse was immediately placed in an ice bath and centrifuged within an hour to obtain a plasma sample. The plasma samples were immediately frozen with liquid nitrogen and stored at −80° C. The stored samples were treated as described in the following (1) or (2), and then the Alb(red) % values of the plasma samples for both the normal rat and the diabetic mouse were calculated.

(1) After freeze-thawing, the sample was immediately diluted 100-fold with 50 mM phosphate buffer (pH 6.0). Then, the solution was placed in a vial, set on an auto sampler set to temperature 4° C., and analyzed by HPLC-ESI-TOFMS.

(2) After freeze-thawing, plasma was incubated at 37° C. for 2 hr. After incubation, a treatment similar to the treatment after freeze-thawing of (1) above was performed. HPLC-ESI-TOFMS and calculation of the Alb(red) % values were performed in the same manner as in Example 1.

With treatment (1), the Alb(red) % was 80.3% for the normal mouse and 80.1% for the diabetic model mouse. On the other hand, with treatment (2), the Alb(red) % value was 72.4±0.8 for the normal mouse and 68.9±1.7 for the diabetic model mouse. As demonstrated, the preincubation treatment resulted in a remarkable difference in Alb(red) % between the samples.

Figure 8:
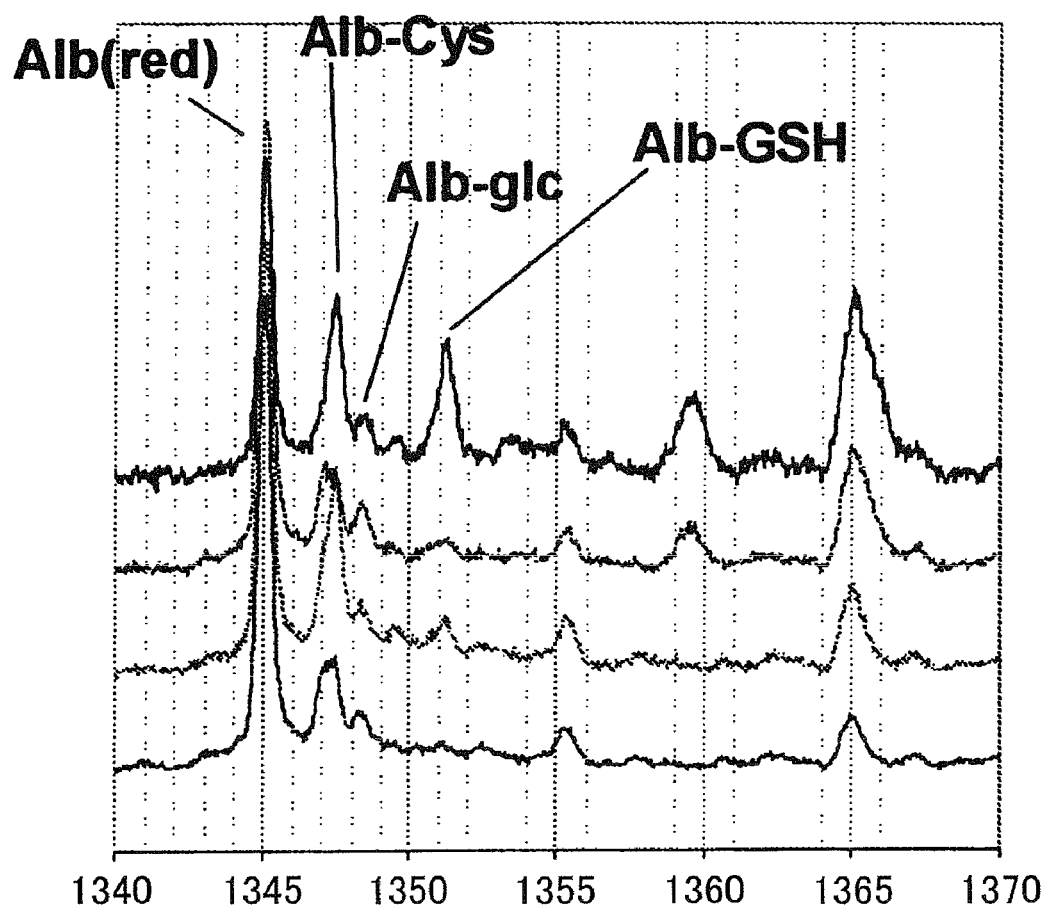
FIG. 8 is a mass spectrum showing the results of Example 4. The data at the top were obtained.

Moreover, a peak derived from glycated albumin was confirmed in addition to the reduced albumin and oxidized albumin (FIG. 8). The proportion of glycated albumin in the total albumin is 9.9% for the normal mouse and 13.9% for the diabetic mouse. Thus, glycated albumin was observed in a greater amount in the diabetic mouse.

EXAMPLE 5

The plasma of a wild-type rat (Sparague-Dawley or F344 rat, male, CLEA Japan, Inc.) was diluted with 50 mM phosphate buffer (pH 6.0). After a filtration with a 0.45 μm filter, the solution was applied to an affinity chromatography Blue HP column equilibrated with 50 mM phosphate buffer. Albumin in the plasma was retained on the column resin, and other contaminants passed through the column or were removed by washing. Lastly, the albumin adsorbed onto the column was eluted with 50 mM phosphate buffer (pH 6.0) containing 1.5 M potassium chloride, which was followed by incubation at 37° C. for 2 hr. The change in Alb(red) % at this time was measured in the same manner as in Example 1, and the results were compared between the Blue HP column-treated sample and the nontreated sample (FIG. 9). As a result, the sample subjected to the Blue HP column showed a smaller change in Alb(red) %. As demonstrated, stabilization of Alb(red) was achieved since affinity chromatography removed the contaminants in the sample.

EXAMPLE 6

The data presented above relate to the stability after plasma separation. In the following Example, the stability of Alb(red) in the blood was examined, since as such is more suitable for clinical tests.

<Sample Treatment>

Blood was collected from healthy volunteers (N=3), and treated by any of the following: 1) addition of heparin, 2) addition of 0.5 M sodium citrate buffer (pH 4.3) to ⅑ volume of the blood, and 3) addition of 75 mM sodium phosphate buffer (pH 6) to 9-fold the volume of blood. Each of these samples was stored in a refrigerator (4° C.).

The blood samples were centrifuged to obtain plasma at the following time points after the treatment: 0, 3, 6, 24, 30, and 48 hrs. Plasma was frozen with liquid nitrogen immediately after collection and stored in a freezer (−80° C.).

<Measurement Method>

Blood which had been treated as described in 1) and 2) above were diluted 100-fold with a dilution solution (50 mM sodium phosphate buffer, pH 6.0), and blood which had been treated as described in 3) was diluted 10-fold with the same dilution solution. The oxidized albumin ratio and reduced albumin ratio were calculated according to HPLC-ESI-TOFMS described in Example 1.

<Measurement Results>

The residual ratio of the reduced albumin ratio (Alb(red) %) was calculated. In sample 1), the residual ratio decreased with the storage time and was 95% at the 48 hr time point. Alternatively, in samples 2) and 3), the residual ratio at the 48 hr time point was 100-101%, with no fluctuation (FIG. 10). It was therefore demonstrated that the fluctuation of the reduced albumin ratio could be suppressed by pH adjustment or dilution.

EXAMPLE 7

The stability of reduced albumin in a sample from blood collection to measurement was examined by the HPLC method in the same manner as in Example 6.

<Sample Treatment>

Blood was collected from healthy volunteers (N=5, samples 1-5), 0.5 M sodium citrate buffer (pH 4.3) was added to the blood at 1/10 the volume of the collected blood, and the mixture was stored in a refrigerator (4° C.).

The blood samples were centrifuged to obtain plasma at the following time points: 0, 24, and 72 hrs after the treatment.

<Measurement Method>

Plasma was diluted 50-fold with 50 mM sodium phosphate buffer (pH 6.0) and subjected to HPLC.

HPLC conditions:

column: ES-502N 7.6 mm i.d.×100 mm DEAE-form (Shodex)

column temperature: 35° C.

Solvent A: 50 mM sodium acetate–400 mM sodium sulfate (pH 4.85)

Solvent B: ethanol

Gradient: A/B=100/0→5 min→100/0→25 min→95/5→5 min→100/0→5 min→100/0

Flow: 1.0 mL/min detection: fluorescence ex. 280 nm em. 340 nm sample injection volume: 20 μL <Measurement Results>

Reduced albumin ratio (HPLC method)

| sample No. | 0 h | 24 h | 72 h |
| --- | --- | --- | --- |
| sample 1 | 77.4% | 77.9% | 77.4% |
| sample 2 | 77.1% | 77.7% | 77.4% |
| sample 3 | 79.6% | 79.9% | 79.4% |
| sample 4 | 77.0% | 77.2% | 76.5% |
| sample 5 | 72.7% | 73.0% | 72.8% |

Residual ratio of reduced albumin ratio (HPLC method)

| sample No. | 0 h | 24 h | 72 h |
| --- | --- | --- | --- |
| sample 1 | 100.0% | 100.6% | 100.0% |
| sample 2 | 100.0% | 100.8% | 100.4% |
| sample 3 | 100.0% | 100.4% | 99.7% |
| sample 4 | 100.0% | 100.3% | 99.4% |
| sample 5 | 100.0% | 100.4% | 100.1% |

The residual ratio of the reduced albumin ratio after 72 hr was 99.4-100.4%, and fluctuation was not observed as compared to the 0 time point. From these results, the stability of reduced albumin up to 72 hr after blood sample collection was confirmed, thus allowing for possible transport of a sample from a hospital to an analytical laboratory.

EXAMPLE 8

In the following Example, the stability of a sample when low-molecular compounds are removed from plasma was confirmed using solid phase extraction.

<Sample Treatment>

Blood was collected from healthy volunteers (N=3, A-C), and treated by any of the following: 1) addition of heparin, or 2) addition of 0.5 M sodium citrate buffer (pH 4.3) in ⅕ the volume of blood, and centrifuged to give plasma components.

<Solid Phase Extraction>

1. 50 mM sodium phosphate buffer (pH 6.0, 1980 uL) was added to plasma (20 µL).

2. A solid phase extraction column (Bond Elut-C18 EWP 200 mg/3 cc) was activated and equilibrated. Activation was performed with 90% acetonitrile (2 mL) containing 0.1% formic acid, and equilibration was performed with water (1 mL).

3. The sample of 1 was applied to the solid phase extraction column of 2.

4. The column was washed with 10% acetonitrile (2 mL) containing 0.1% formic acid, and albumin was eluted with 90% acetonitrile (1 mL) containing 0.1% formic acid.

5. The eluate of 4 was immediately subjected to ESI-TOFMS as follows.

<ESI-TOFMS Measurement Conditions>

Eluent: 90% Acetonitrile containing 0.1% formic acid was applied at a flow rate of 15 µL/min and, using an auto sampler, the sample (1 µL) was injected into an ESI-TOFMS according to the flow-injection method. The MS conditions for the measurement were the same as those of the MS segment of the HPLC-ESI-TOFMS described in Example 1.

<Measurement Results>

According to the above, plasma was obtained from human blood, which was then subjected to solid phase extraction. The stability thereof in the autosampler for the ESI-TOFMS measurement was examined. The residual ratio of the reduced albumin ratio (%) was measured at day 0, day one, and day two, as shown in the following table.

|  | heparin added collected plasma + solid phase extraction | | | citric acid Na added collected plasma + solid phase extraction | | |
| --- | --- | --- | --- | --- | --- | --- |
|  | A | B | C | A | B | C |
| Day 0 | 100.0 | 100.0 | 100.0 | 100.0 | 100.0 | 100.0 |
| Day 1 | 100.5 | 100.4 | 100.3 | 100.4 | 100.4 | 100.4 |
| Day 2 | 100.8 | 100.8 | 100.6 | 100.7 | 100.7 | 100.6 |

Blood treated as described in 1) and 2) above were both stable on the auto sampler for two days. Accordingly, regardless of the blood collection methods, solid phase extraction showed that the blood samples were stable for two days before analysis. From the results, it is clear that removal of low-molecular compounds in the plasma by chromatography suppresses formation of oxidized albumin, and enables stable analysis. The results of this Example demonstrate stability of the analytical method of the present invention.

Furthermore, assuming actual blood collection at hospitals and the like, the plasma preservation stability was confirmed according to the solid phase extraction method.

<Sample Treatment>

Blood was collected from healthy volunteers (N=3), and treated with any of the following: 1) addition of heparin or 2) addition of 0.5 M sodium citrate buffer (pH 4.3) to ⅕ of the volume of the blood, and centrifuged to obtain plasma.

Immediately after obtaining the plasma, the plasma was stored in a refrigerator for either one day or two. Then, the plasma was subjected to solid phase extraction in the same manner as above, and then to ESI-TOFMS measurement.

<Measurement Results (FIG. 11)>

The residual ratio of the reduced albumin ratio (Alb(red) %) was calculated. For the blood treated as described in 1), the residual ratio decreased the longer it was stored, in that it became 92-94% after 2 days. Alternatively, for the blood treated as described above in 2), the residual ratio after storage for 2 days was 100-101%, with no fluctuation as compared to that that was measured immediately after the treatment. These results clearly demonstrate that reduced albumin remained stable for 2 days with refrigeration, due to the adjustment of the pH. Moreover, when using the flow-injection method when solid phase extraction and ESI-MS are combined, the measurement time can be drastically reduced as evidenced by the MS measurement time of not more than 5 min.

EXAMPLE 9

In this Example, a method for preparing a reduced or oxidized albumin standard sample is described.

Blood was collected from healthy volunteers, and plasma was obtained. From the plasma, albumin was purified by affinity chromatography according to the procedures shown in Example 5. The purified eluate was diluted to 4 mg/mL with 50 mM phosphate buffer containing 1.5 M potassium chloride (pH 6.0). This was used as a reduced albumin standard sample. A thiol group-containing low-molecular compound such as cysteine, cystine, homocysteine, homocystine, reduced glutathione, oxidized reduced glutathione, or oxidized glutathione was added to the solution to give an oxidized albumin standard sample. Cystine and homocystine are the oxidized forms of cysteine and homocysteine, respectively.

3 kinds of cysteine-added albumin, homocysteine-added albumin, and glutathione-added albumin were respectively prepared as follows to obtain oxidized albumins as they exist in the living body.

For preparing cysteine-added albumin, a 4 mg/mL purified albumin solution (120 mL) was mixed with a 0.6 mM aqueous cysteine (manufactured by Sigma Ltd.) solution (12 mL) and a 0.6 mM aqueous cystine (manufactured by Sigma Ltd.) solution (108 mL).

To prepare homocysteine-added albumin, a 4 mg/mL purified albumin solution (120 mL) was mixed with a 3 mM aqueous homocysteine (manufactured by Sigma Ltd.) solution (8 mL) and a 3 mM aqueous homocystine (manufactured by Sigma Ltd.) solution (72 mL).

To prepare glutathione-added albumin, a 4 mg/mL purified albumin solution (120 mL) was mixed with a 3 mM aqueous reduced glutathione (manufactured by Wako Pure Chemical Industries, Ltd.) solution (8 mL) and a 3 MM aqueous oxidized glutathione (manufactured by Wako Pure Chemical Industries, Ltd.) solution (72 mL).

Every prepared solution was divided and placed in several Falcon tubes (50 cc size), and the tubes were flushed with argon gas. The tubes were left standing in a 37° C. incubator (horizontally placed) for 48 hr. After completion of the reaction, excess thiol group-containing low-molecular compounds and their oxidants were removed and the solution was concentrated by ultrafiltration using Microcon YM-30 (500 µL size: manufactured by MILLIPORE). The solution was centrifuged at 2000 rpm and the buffer was exchanged with a 50 mM phosphate buffer containing 0.9 w/v % sodium chloride (pH 7.3). The steps (1) albumin solution concentration, (2) removal of filtration solution, and (3) charging with 50 mM phosphate buffer containing 0.9 w/v % sodium chloride (pH 7.3) were repeated 15 times or more to remove the thiol group-containing low-molecular compounds and their oxidants from the prepared solution.

The purity (%) of the reduced or oxidized albumin in the oxidized albumin standard samples (3 kinds) obtained by this method (proportion of reduced or oxidized albumin relative to the total amount of reduced albumin and oxidized albumin) was determined by HPLC-ESI-TOFMS as described in Example 1 (FIG. 12). As a result, the purity of the oxidized albumin in the cysteine-added albumin ([B] in FIG. 12), homocysteine-added albumin ([C] in FIG. 12) and glutathione-added albumin ([D] in FIG. 12) was 95%, 96% and 65%, respectively. On the other hand, the purity of the reduced albumin in the reduced albumin standard sample ([A] in FIG. 12) was 78%.

The stability of the reduced albumin standard solution and various oxidized albumin standards prepared according to the above-mentioned methods were evaluated after storage at 4° C., −20° C. and −80° C. Sampling was conducted at regular intervals, and changes in the purity were measured using HPLC-ESI-TOFMS as described in Example 1.

Storage stability of reduced albumin and oxidized albumin standards (purity change rate %)

|  | day 0 | day 21 | day 44 | day 91 |
|---|---|---|---|---|
| reduced albumin | | | | |
| 4° C. | 100.0 | 100.3 | 97.8 | 100.8 |
| −20° C. | 100.0 | 100.4 | 97.8 | 100.9 |
| −80° C. | 100.0 | 101.2 | 98.4 | 102.0 |
| cysteine added oxidized albumin | | | | |
| 4° C. | 100.0 | 99.5 | 100.9 | 99.9 |
| −20° C. | 100.0 | 101.9 | 101.5 | 103.0 |
| −80° C. | 100.0 | 101.9 | 101.8 | 102.8 |
| homocysteine added oxidized albumin | | | | |
| 4° C. | 100.0 | 100.1 | 98.5 | 100.8 |
| −20° C. | 100.0 | 100.2 | 99.2 | 101.5 |
| −80° C. | 100.0 | 100.2 | 99.8 | 101.6 |
| glutathione added oxidized albumin | | | | |
| 4° C. | 100.0 | 102.7 | 103.3 | 103.2 |
| −20° C. | 100.0 | 101.3 | 102.7 | 104.3 |
| −80° C. | 100.0 | 100.8 | 101.4 | 101.9 |

As a result, the purity of the oxidized albumin standards hardly changed at all temperatures, thereby demonstrating the preservation stability of the oxidized albumin standards.

In addition, albumin was analyzed by HPLC as described in Example 7, and using the prepared standards. The analyzed values of the purity of reduced albumin, cysteine-added albumin, and glutathione-added albumin matched well with the values measured by ESI-TOFMS, but with higher accuracy. Therefore, the accuracy of the HPLC method could be guaranteed by using the albumin standards of the present invention.

|  | ESI-TOFMS method | HPLC method |
|---|---|---|
| reduced albumin standard sample | reduced albumin purity 75% | reduced albumin purity 76% |
| oxidized albumin standard sample | oxidized albumin purity 95% | oxidized albumin purity 95% |

INDUSTRIAL APPLICABILITY

According to the present invention, since the amount and ratio of reduced/oxidized albumins and glycated protein components can be conveniently measured with high sensitivity, a method useful for biochemical study, diagnosis of diseases, and screening for pharmaceutical agents is provided. In particular, since the ratios of reduced/oxidized albumins and glycated protein components can be conveniently measured with high sensitivity, various conditions associated with oxidative stress, such as hepatic disease, renal disease, diabetes, rheumatism, encephalopathy, fatigue, aging, oxidative stress, cardiac disease, lung disease, and the like can be preferably analyzed.

While some of the embodiments of the present invention have been described in detail in the above, it is, however, possible to make various modifications and changes to the particular embodiments shown without substantially departing from the teaching and advantages of the present invention. Such modifications and changes are encompassed in the spirit and scope of the present invention as set forth in the appended claims.

We claim:

1. A method of analyzing albumin in a sample solution taken from a test subject, the method comprising the following steps:
    A) forming the sample solution by diluting a sample comprising albumin 50- to 100000-fold with a buffer,
    B) adjusting the pH of the sample solution to pH 4-9 with a buffer,
    C) incubating the sample solution of step B) at an incubation temperature of between 4-60° C. for at least 2 hours,
    D) after step C), subjecting the sample solution to either mass spectrometry, liquid chromatography, or both, and
    E) determining the amount of reduced albumin and oxidized albumin, and/or the ratio of reduced albumin to oxidized albumin in the sample solution;
    wherein said sample solution is selected from the group consisting of blood and plasma.

2. The method of claim 1, wherein step D) is performed within 100 hr after the completion of step B).

3. The method of claim 1, wherein the buffer is selected from the group consisting phosphate buffer, Tris-HCl buffer, borate buffer, citrate buffer, acetate buffer, carbonate buffer, HEPES buffer, succinate buffer, and combinations thereof.

4. The method of claim 1, comprising subjecting the sample solution to ultrafiltration before step D).

5. The method of claim 1, comprising subjecting the sample solution to purification by chromatography before step D).

6. The method of claim 5, wherein the chromatography is selected from the group consisting of high performance liquid chromatography, reversed phase chromatography, normal phase chromatography, affinity chromatography, ion exchange chromatography, gel filtration chromatography, hydrophobic chromatography, and combinations thereof.

7. The method of claim 1, wherein the mass spectrometry is performed using an apparatus selected from the group consisting of an electrospray ionization time-of-flight mass spectrometer, a quadrupole mass spectrometer, an ion trap mass spectrometer, a Fourier transform ion cyclotron mass spectrometer, a matrix-assisted laser desorption-ionization time-of-flight mass spectrometer, a magnetic sector-type mass spectrometer, a tandem quadrupole mass spectrometer, and combinations thereof.

8. The method of claim 1, wherein the test subject has, or is suspected of having, a condition selected from the group consisting of a hepatic disease, a renal disease, diabetes, rheumatism, encephalopathy, fatigue, aging, oxidative stress, a cardiac disease, a lung disease, and combinations thereof.

9. A method of analyzing blood or plasma taken from a test subject who has, or is suspected of having, a condition selected from the group consisting of a hepatic disease, a renal disease, diabetes, rheumatism, encephalopathy, fatigue, aging, oxidative stress, a cardiac disease, a lung disease, and combinations thereof, the method comprising:

analyzing the amount of reduced albumin and oxidized albumin, and/or the ratio of reduced albumin to oxidized albumin in blood or plasma taken from the test subject according to the method of claim 1.

10. A method of screening a test substance, the method comprising

A) measuring the amount of reduced albumin and oxidized albumin, and/or the ratio of reduced albumin to oxidized albumin in sample solutions from a test subject both with and without administration of a test substance, said measuring comprising analyzing according to claim 1;
  B) comparing the amount and/or the ratio obtained with administration of the test substance and the amount and/or ratio obtained without administration of the test substance; and
  selecting a sample having a greater amount and/or ratio of reduced albumin with administration of the test substance as compared to non-administration of the test substance.

11. The method of claim 10, wherein the test substance is an antioxidant.

12. The method of claim 1, wherein step D) is performed within 72 hours after the completion of step B).

13. The method of claim 1, wherein step D) is performed between 2 and 12 hours after the completion of step B).

14. The method of claim 1, wherein the incubation temperature is between 4-40° C.

15. The method of claim 9, wherein the sample solution is incubated prior to step A), and wherein the method further comprises the step:

F) comparing the amount or ratio determined in step E) with that in blood or plasma taken from a control.

* * * * *